(12) United States Patent
Werling et al.

(10) Patent No.: US 7,193,084 B2
(45) Date of Patent: Mar. 20, 2007

(54) POLYMORPHIC FORM OF ITRACONAZOLE

(75) Inventors: Jane Werling, Arlington Heights, IL (US); Mark J. Doty, Grayslake, IL (US); Christine L. Rebbeck, Algonquin, IL (US); Joseph Chung Tak Wong, Gurnee, IL (US); James E. Kipp, Wauconda, IL (US)

(73) Assignee: Baxter International Inc., Deerfield, IL (US)

( * ) Notice: Subject to any disclaimer, the term of this patent is extended or adjusted under 35 U.S.C. 154(b) by 903 days.

(21) Appl. No.: 10/213,352

(22) Filed: Aug. 5, 2002

(65) Prior Publication Data

US 2003/0100568 A1    May 29, 2003

Related U.S. Application Data

(63) Continuation-in-part of application No. 10/035,821, filed on Oct. 19, 2001, which is a continuation-in-part of application No. 09/953,979, filed on Sep. 17, 2001, which is a continuation-in-part of application No. 09/874,637, filed on Jun. 5, 2001, now Pat. No. 6,869,617.

(60) Provisional application No. 60/258,160, filed on Dec. 22, 2000.

(51) Int. Cl.
    *C07D 403/00*    (2006.01)
    *A61K 31/497*    (2006.01)

(52) U.S. Cl. ............... 544/366; 544/358; 514/254.07; 514/254.05

(58) Field of Classification Search ............... 544/366, 544/358, 359; 514/254.07, 254.05
    See application file for complete search history.

(56) References Cited

U.S. PATENT DOCUMENTS

| | | | |
|---|---|---|---|
| 2,745,785 A | 1/1956 | Bruce et al. | 514/192 |
| 4,056,635 A | 11/1977 | Glen et al. | 424/346 |
| 4,073,943 A | 2/1978 | Wretlind et al. | 514/772 |
| 4,452,817 A | 6/1984 | Glen et al. | 424/346 |
| 4,540,602 A | 9/1985 | Motoyama et al. | 427/213.31 |
| 4,606,940 A | 8/1986 | Frank et al. | |
| 4,608,278 A | 8/1986 | Frank et al. | 427/213.35 |
| 4,622,219 A | 11/1986 | Haynes | 424/38 |
| 4,725,442 A | 2/1988 | Haynes | 424/490 |
| 4,798,846 A | 1/1989 | Glen et al. | 514/713 |
| 4,826,689 A | 5/1989 | Violanto | 424/489 |
| 4,973,465 A | 11/1990 | Baurain et al. | 424/406 |
| 4,997,454 A | 3/1991 | Violante et al. | 23/305 A |
| 5,023,271 A | 6/1991 | Vigne et al. | 514/458 |
| 5,049,322 A | 9/1991 | Devissaguet et al. | |
| 5,078,994 A | 1/1992 | Nair et al. | 424/501 |
| 5,091,187 A | 2/1992 | Haynes | 424/450 |
| 5,091,188 A | 2/1992 | Haynes | 424/450 |
| 5,100,591 A | 3/1992 | Laclef et al. | 264/4.6 |
| 5,118,528 A | 6/1992 | Fessi et al. | 427/213.36 |
| 5,122,543 A | 6/1992 | Khanna | |
| 5,133,908 A | 7/1992 | Stainmesse et al. | 264/4.1 |
| 5,145,684 A | 9/1992 | Liversidge et al. | 424/489 |
| 5,151,264 A | 9/1992 | Samain et al. | |
| 5,152,923 A | 10/1992 | Weder et al. | 252/312 |
| 5,174,930 A | 12/1992 | Stainmesse et al. | |
| 5,188,837 A | 2/1993 | Domb | 424/450 |
| 5,246,707 A | 9/1993 | Haynes | 424/450 |
| 5,250,236 A | 10/1993 | Gasco | 264/4.4 |
| 5,269,979 A | 12/1993 | Fountain | |
| 5,298,262 A | 3/1994 | Na et al. | 424/489 |
| 5,302,401 A | 4/1994 | Liversidge et al. | 424/501 |
| 5,314,506 A | 5/1994 | Midler, Jr. et al. | |
| 5,318,767 A | 6/1994 | Liversidge | |
| 5,326,552 A | 7/1994 | Na et al. | 424/4 |
| 5,336,507 A | 8/1994 | Na et al. | 424/489 |
| 5,340,564 A | 8/1994 | Illig et al. | 424/9 |
| 5,346,702 A | 9/1994 | Na et al. | 424/490 |
| 5,352,459 A | 10/1994 | Hollister et al. | 424/489 |
| 5,354,563 A | 10/1994 | Toyotama | |
| 5,389,263 A | 2/1995 | Gallagher et al. | 210/729 |
| 5,399,363 A | 3/1995 | Liversidge et al. | 424/490 |
| 5,417,956 A | 5/1995 | Moser | |
| 5,429,824 A | 7/1995 | June | 424/489 |
| 5,447,710 A | 9/1995 | Na et al. | 424/9.455 |
| 5,466,646 A | 11/1995 | Moser | |
| 5,470,583 A | 11/1995 | Na et al. | 424/489 |
| 5,474,989 A | 12/1995 | Hashimoto et al. | |
| 5,494,683 A | 2/1996 | Liversidge et al. | 424/490 |
| 5,510,118 A | 4/1996 | Bosch et al. | 424/489 |
| 5,518,187 A | 5/1996 | Bruno et al. | |
| 5,518,738 A | 5/1996 | Eickhoff et al. | 424/493 |
| 5,534,270 A | 7/1996 | De Castro | 424/490 |
| 5,543,133 A | 8/1996 | Swanson et al. | 424/9.45 |
| RE35,338 E | 9/1996 | Haynes | |
| 5,552,160 A | 9/1996 | Liversidge et al. | 424/489 |
| 5,560,932 A | 10/1996 | Bagchi et al. | 424/489 |
| 5,560,933 A | 10/1996 | Soon-Shiong et al. | 424/489 |

(Continued)

FOREIGN PATENT DOCUMENTS

| | | |
|---|---|---|
| EP | 0379 379 B1 | 1/1990 |
| EP | 0498482 B1 | 8/1992 |
| EP | 0499299 B1 | 8/1992 |

(Continued)

OTHER PUBLICATIONS

The Merck Index (Abstract of The Merck Index, 12th edition 1996, pp. 894-895) (Abstract Sent).*

(Continued)

*Primary Examiner*—Samuel Barts
*Assistant Examiner*—Michael C. Henry
(74) *Attorney, Agent, or Firm*—Michael C. Mayo; Raymond M. Mehler

(57) ABSTRACT

The present invention provides a polymorphic form of itraconazole.

3 Claims, 18 Drawing Sheets

U.S. PATENT DOCUMENTS

| | | | |
|---|---|---|---|
| 5,565,383 A | 10/1996 | Sakai | 437/200 |
| 5,569,448 A | 10/1996 | Wong et al. | 424/9.45 |
| 5,573,783 A | 11/1996 | Desieno et al. | 424/490 |
| 5,578,325 A | 11/1996 | Domb et al. | 424/501 |
| 5,580,579 A | 12/1996 | Ruddy et al. | 424/489 |
| 5,587,143 A | 12/1996 | Wong | 424/9.1 |
| 5,591,456 A | 1/1997 | Franson et al. | |
| 5,605,785 A | 2/1997 | Texter et al. | 430/546 |
| 5,626,864 A | 5/1997 | Rosenberg et al. | |
| 5,635,609 A | 6/1997 | Levy et al. | |
| 5,641,515 A | 6/1997 | Ramtoola | 424/189 |
| 5,641,745 A | 6/1997 | Ramtoola | |
| 5,660,858 A | 8/1997 | Parikh et al. | 424/450 |
| 5,662,883 A | 9/1997 | Bagchi et al. | 424/9.4 |
| 5,662,932 A | 9/1997 | Amselem et al. | 424/450 |
| 5,665,331 A | 9/1997 | Bagchi et al. | 424/9.45 |
| 5,665,383 A | 9/1997 | Grinstaff et al. | 424/450 |
| 5,707,634 A | 1/1998 | Schmitt | |
| 5,716,642 A | 2/1998 | Bagchi et al. | 424/489 |
| 5,720,551 A | 2/1998 | Shechter | 366/147 |
| 5,766,635 A | 6/1998 | Spenleuhauer et al. | 424/489 |
| 5,780,062 A | 7/1998 | Frank et al. | 424/501 |
| 5,833,891 A | 11/1998 | Subramaniam et al. | 264/7 |
| 5,858,410 A | 1/1999 | Muller et al. | 424/489 |
| 5,862,999 A | 1/1999 | Czekai et al. | |
| 5,874,111 A | 2/1999 | Maitra et al. | 424/499 |
| 5,916,583 A | 6/1999 | Broberg et al. | |
| 5,916,596 A | 6/1999 | Desai et al. | 424/489 |
| 5,922,355 A | 7/1999 | Parikh et al. | 424/489 |
| 5,939,100 A | 8/1999 | Albrechtsen et al. | |
| 5,981,719 A | 11/1999 | Woiszwillo et al. | 530/410 |
| 5,989,583 A | 11/1999 | Amselem | |
| 6,007,845 A | 12/1999 | Domb et al. | 424/501 |
| 6,039,981 A | 3/2000 | Woo et al. | |
| 6,045,826 A | 4/2000 | Borowy-Borowski et al. | |
| 6,045,829 A | 4/2000 | Liversidge et al. | 424/489 |
| 6,048,550 A | 4/2000 | Chan et al. | 424/497 |
| 6,063,138 A | 5/2000 | Hanna et al. | |
| 6,063,910 A | 5/2000 | Debenedetti et al. | 530/418 |
| 6,068,858 A | 5/2000 | Liversidge et al. | 424/489 |
| 6,086,376 A | 7/2000 | Moussa et al. | 434/45 |
| 6,090,925 A | 7/2000 | Woiszwillo et al. | 530/410 |
| 6,090,983 A | 7/2000 | Yokoyama et al. | 564/346 |
| 6,132,750 A | 10/2000 | Perrier et al. | 424/418 |
| 6,139,870 A | 10/2000 | Verrecchia | |
| 6,143,211 A | 11/2000 | Mathiowitz et al. | 264/4 |
| 6,146,663 A | 11/2000 | Bissery et al. | 424/489 |
| 6,153,225 A | 11/2000 | Lee et al. | 424/501 |
| 6,165,506 A | 12/2000 | Jain et al. | 424/466 |
| 6,177,103 B1 | 1/2001 | Pace et al. | 424/489 |
| 6,197,757 B1 | 3/2001 | Perrier et al. | 514/53 |
| 6,207,134 B1 | 3/2001 | Fahlvik et al. | |
| 6,207,178 B1 | 3/2001 | Westesen et al. | |
| 6,214,384 B1 | 4/2001 | Pallado et al. | 424/493 |
| 6,217,886 B1 | 4/2001 | Onyuksel et al. | 424/401 |
| 6,221,332 B1 | 4/2001 | Thumm et al. | |
| 6,221,398 B1 | 4/2001 | Jakupovic et al. | |
| 6,221,400 B1 | 4/2001 | Liversidge et al. | 424/489 |
| 6,228,399 B1 | 5/2001 | Parikh et al. | 424/489 |
| 6,231,890 B1 | 5/2001 | Naito et al. | |
| 6,235,224 B1 | 5/2001 | Mathiowitz | 264/4 |
| 6,238,677 B1 | 5/2001 | Fanta et al. | 424/400 |
| 6,238,694 B1 | 5/2001 | Gasco | 424/450 |
| 6,245,349 B1 | 6/2001 | Yiv et al. | 424/450 |
| 6,248,363 B1 | 6/2001 | Patel et al. | 424/497 |
| 6,264,922 B1 | 7/2001 | Wood et al. | 424/45 |
| 6,267,989 B1 | 7/2001 | Liversidge | 424/489 |
| 6,268,053 B1 | 7/2001 | Woiszwillo et al. | 428/402 |
| 6,270,806 B1 | 8/2001 | Liversidge et al. | 424/497 |
| 6,294,204 B1 | 9/2001 | Rossling et al. | 424/497 |
| 6,299,906 B1 | 10/2001 | Bausch et al. | 424/489 |
| 6,306,406 B1 | 10/2001 | Deluca | |
| 6,337,092 B1 | 1/2002 | Khan et al. | 424/489 |
| 6,344,271 B1 | 2/2002 | Yadav et al. | |
| 6,346,533 B1 | 2/2002 | Cha et al. | 514/245.05 |
| 6,365,191 B1 | 4/2002 | Burman et al. | |
| 6,375,986 B1 | 4/2002 | Ryde et al. | |
| 6,395,300 B1 | 5/2002 | Straub et al. | |
| 6,428,814 B1 | 8/2002 | Bosch et al. | |
| 6,462,093 B1 | 10/2002 | Miyamoto et al. | |
| 6,607,784 B2 | 8/2003 | Kipp et al. | |
| 2001/0007678 A1 | 7/2001 | Baert et al. | |
| 2001/0025058 A1 | 9/2001 | Borowy-Borowski et al. | |
| 2001/0042932 A1 | 11/2001 | Mathiowitz et al. | |
| 2002/0012675 A1 | 1/2002 | Jain et al. | |
| 2002/0012704 A1 | 1/2002 | Pace et al. | |
| 2002/0041896 A1 | 4/2002 | Straub et al. | |
| 2002/0048610 A1 | 4/2002 | Cima et al. | |
| 2002/0054912 A1 | 5/2002 | Kim et al. | |
| 2002/0110599 A1 | 8/2002 | Auweter et al. | |
| 2002/0127278 A1 | 9/2002 | Kipp et al. | |
| 2002/0168402 A1 | 11/2002 | Kipp et al. | |
| 2003/0003155 A1 | 1/2003 | Kipp et al. | |
| 2003/0031719 A1 | 2/2003 | Kipp et al. | |
| 2003/0044433 A1 | 3/2003 | Werling et al. | |
| 2003/0059472 A1 | 3/2003 | Brynjelsen et al. | |
| 2003/0072807 A1 | 4/2003 | Wong et al. | |
| 2003/0077329 A1 | 4/2003 | Kipp et al. | |
| 2003/0096013 A1 | 5/2003 | Werling et al. | |
| 2003/0170279 A1 | 9/2003 | Lambert et al. | |
| 2003/0206959 A9 | 11/2003 | Kipp et al. | |
| 2004/0022862 A1 | 2/2004 | Kipp et al. | |

FOREIGN PATENT DOCUMENTS

| | | |
|---|---|---|
| EP | 0517565 B1 | 12/1992 |
| EP | 0349 428 B1 | 1/1993 |
| EP | 0377 477 B1 | 3/1993 |
| EP | 0535534 A1 | 4/1993 |
| EP | 0169 618 B2 | 11/1993 |
| EP | 0577215 A1 | 5/1994 |
| EP | 0600532 A2 | 6/1994 |
| EP | 0600532 A3 | 6/1994 |
| EP | 0601618 A2 | 6/1994 |
| EP | 0601618 A3 | 6/1994 |
| EP | 0601619 A2 | 6/1994 |
| EP | 0601619 A3 | 6/1994 |
| EP | 0602700 A2 | 6/1994 |
| EP | 0602700 A3 | 6/1994 |
| EP | 0602702 A1 | 6/1994 |
| EP | 0605024 A2 | 7/1994 |
| EP | 0605024 A3 | 7/1994 |
| EP | 0207 134 B1 | 8/1994 |
| EP | 0275 796 B2 | 9/1995 |
| EP | 0820 300 B1 | 4/1996 |
| EP | 0372 070 B1 | 1/1997 |
| EP | 0754034 B1 | 1/1997 |
| EP | 0644 755 A1 | 3/1997 |
| EP | 0832 569 A2 | 4/1998 |
| EP | 0730 406 B1 | 7/1998 |
| EP | 0498482 B1 | 9/1999 |
| EP | 0831 770 B1 | 8/2000 |
| EP | 0988 863 A3 | 8/2000 |
| EP | 0499299 B1 | 8/2000 |
| EP | 0517565 B1 | 10/2000 |
| EP | 0808154 B1 | 12/2000 |
| EP | 0720 471 B1 | 4/2001 |
| EP | 0804162 B1 | 9/2001 |
| EP | 0828 479 B1 | 10/2001 |
| EP | 0788 350 B1 | 2/2002 |
| EP | 0752 245 B1 | 5/2002 |
| EP | 1210 942 A2 | 6/2002 |
| EP | 1012 204 B1 | 1/2003 |
| EP | 1156 788 A1 | 1/2003 |

| | | | |
|---|---|---|---|
| EP | 1105 109 B1 | 4/2003 | |
| EP | 0812 187 A1 | 5/2003 | |
| EP | 0832 569 B1 | 11/2003 | |
| JP | 02306902 | 12/1990 | |
| JP | H2-306902 | 12/1990 | |
| WO | WO 85/00011 A1 | 1/1985 | |
| WO | WO 86/03676 A1 | 7/1986 | |
| WO | WO 89/11850 A1 | 12/1989 | |
| WO | WO 90/03782 A2 | 4/1990 | |
| WO | WO 90/15593 A1 | 12/1990 | |
| WO | WO 91/06292 A1 | 5/1991 | |
| WO | WO 91/12794 A1 | 9/1991 | |
| WO | WO 91/16068 A1 | 10/1991 | |
| WO | WO 92/00731 A1 | 1/1992 | |
| WO | WO 92/03380 A1 | 3/1992 | |
| WO | WO 93/25190 A1 | 12/1993 | |
| WO | WO 94/20072 A1 | 9/1994 | |
| WO | WO 95/05164 A1 | 2/1995 | |
| WO | WO 95/27482 A1 | 10/1995 | |
| WO | WO 96/00567 A1 | 1/1996 | |
| WO | WO 96/14833 A1 | 5/1996 | |
| WO | WO 96/20698 A2 | 7/1996 | |
| WO | WO 97/03657 A1 | 7/1996 | |
| WO | WO 96/24336 A1 | 8/1996 | |
| WO | WO 96/24340 A1 | 8/1996 | |
| WO | WO 96/25150 A1 | 8/1996 | |
| WO | WO 96/25152 A1 | 8/1996 | |
| WO | WO 96/25918 A1 | 8/1996 | |
| WO | WO 96/31231 A1 | 10/1996 | |
| WO | WO 97/14407 A1 | 4/1997 | |
| WO | WO 97/30695 A1 | 8/1997 | |
| WO | WO 97/36611 A1 | 10/1997 | |
| WO | WO 97/41837 A2 | 11/1997 | |
| WO | WO 97/44014 A1 | 11/1997 | |
| WO | WO 98/07410 A1 | 2/1998 | |
| WO | WO 98/07414 A1 | 2/1998 | |
| WO | WO 98/14174 A1 | 4/1998 | |
| WO | WO 98/14180 A1 | 4/1998 | |
| WO | WO 98/35666 A1 | 8/1998 | |
| WO | WO 98/57967 | * 12/1998 | |
| WO | WO 98/57967 A1 | 12/1998 | |
| WO | WO 99/00113 A1 | 1/1999 | |
| WO | WO 99/02665 A1 | 1/1999 | |
| WO | WO 99/03450 A1 | 1/1999 | |
| WO | WO 99/16443 A1 | 4/1999 | |
| WO | WO 99/29316 A1 | 6/1999 | |
| WO | WO 99/30833 A1 | 6/1999 | |
| WO | WO 99/32156 A2 | 7/1999 | |
| WO | WO 99/33467 A1 | 7/1999 | |
| WO | WO 99/38493 A1 | 8/1999 | |
| WO | WO 99/49846 A2 | 10/1999 | |
| WO | WO 99/49848 A1 | 10/1999 | |
| WO | WO 99/59550 A | 11/1999 | |
| WO | WO 99/61001 A1 | 12/1999 | |
| WO | WO 99/65469 A3 | 12/1999 | |
| WO | WO 00/09096 B1 | 2/2000 | |
| WO | WO 00/12124 A1 | 3/2000 | |
| WO | WO 00/12125 A1 | 3/2000 | |
| WO | WO 00/18374 A1 | 4/2000 | |
| WO | WO 00/27363 A1 | 5/2000 | |
| WO | WO 00/30615 A1 | 6/2000 | |
| WO | WO 00/30616 A1 | 6/2000 | |
| WO | WO 00/37050 A1 | 6/2000 | |
| WO | WO 00/40220 A1 | 7/2000 | |
| WO | WO 00/51572 B1 | 9/2000 | |
| WO | WO 00/71079 A2 | 11/2000 | |
| WO | WO 01/12155 A1 | 2/2001 | |
| WO | WO 01/17546 A1 | 3/2001 | |
| WO | WO 01/21154 A2 | 3/2001 | |
| WO | WO 01/21154 A3 | 3/2001 | |
| WO | WO 02/21154 A3 | 3/2001 | |
| WO | WO 01/26635 A2 | 4/2001 | |
| WO | WO 01/62374 A2 | 8/2001 | |
| WO | WO 01/64164 A2 | 9/2001 | |
| WO | WO 01/80828 A2 | 11/2001 | |
| WO | WO 01/85345 A1 | 11/2001 | |
| WO | WO 1/87264 A2 | 11/2001 | |
| WO | WO 02/17883 A2 | 3/2002 | |
| WO | WO 02/24163 A1 | 3/2002 | |
| WO | WO 02/24169 A1 | 3/2002 | |
| WO | WO 02/43702 A2 | 6/2002 | |
| WO | WO 02/51386 A2 | 7/2002 | |
| WO | WO 02/55059 A2 | 7/2002 | |
| WO | WO 02/60411 A2 | 8/2002 | |
| WO | WO 02/72070 A1 | 9/2002 | |
| WO | WO 02/72071 A1 | 9/2002 | |
| WO | WO 02/74282 A1 | 9/2002 | |
| WO | WO 02/080678 A1 | 10/2002 | |
| WO | WO 02/80883 A2 | 10/2002 | |
| WO | WO 02/89773 A2 | 11/2002 | |
| WO | WO 03/26611 A2 | 4/2003 | |
| WO | WO 03/26611 A3 | 4/2003 | |
| WO | WO 03/35031 A1 | 5/2003 | |
| WO | WO 03/045330 A2 | 6/2003 | |
| WO | WO 03/045330 A3 | 6/2003 | |
| WO | WO 04/103348 A2 | 12/2004 | |
| WO | WO 04/103348 A3 | 12/2004 | |

OTHER PUBLICATIONS

PCT/US2004/036604 International Search Report, dated Mar. 22, 2005.

B. Sjostrom et al., "The Formation of Submicron Organic Particles by Precipitation in an Emulsion", J.Dispersion Science and Technology, 15(1), 89-117 (1994).

Avanti Polar Lipids, Inc.., website printout, www.avantilipids.com, "Synthetic Products—Functionalized Phospholipids: Lipids for Conjugation of Proteins/Peptides/Drugs to Liposomes" (7 pgs), Mar. 2003.

Avanti Polar Lipids, Inc.., website printout, www.avantilipids.com, "Polymer and Polymerizable Lipids: Functionalized PEG Lipids" (3 pgs), Mar. 2003.

Avanti Polar Lipids, Inc.., website printout, www.avantilipids.com, "Polymer and Polymerizable Lipids: Poly(ethylene glycol)-Lipid Conjugates" (8 pgs) , Mar. 2003.

Davis et al., "Pulmonary Perfusion Imaging: Acute Toxicity and Safety Factors as a Function of Particle Size", J.Nucl Med., vol. 19 (1978), pp. 1209-1213.

Schroeder et al., "Physiological Effects of Subvisible Microspheres Administered Intravenously to Beagle Dogs", Journal of Pharmaceutical Sciences, vol. 67, No. 4, Apr. 1978, pp. 508-512.

Yokel et al., "Acute Toxicity of Latex Microspheres", Toxicity Letters, vol. 9 (1981), pp. 165-170.

Allen et al., "Critical Evaluation of Acute Cardiopulmonary Toxicity of Microspheres", J.Nucl Med., vol. 19 (1987), pp. 1204-1208.

B. Sjostrom et al., "Preparation Of Submicron Drug Particles In Lecithin-Stabilized O/W Emulsions I. Model Studies Of The Precipitation Of Cholesteryl Acetate", Int. J. Pharm., 88 (1992) pp. 53-62.

B. Sjostrom et al., "A Method For The Preparation Of Submicron Particles Of Sparingly Water-Soluble Drugs By Precipitation In Oil-In-Water Emulsions. II: Influence Of The Emulsifier, The Solvent And The Drug Substance", J. Pharm. Sci., 82(6), (1992) pp. 584-589.

Duncker and Reichelt, "Effects of the Pharmaceutical Cosolvent hydroxypropyl-beta-cyclodextrin on Porcine Corneal Endothelium", Graef's Archive for Clinical and Experimental Ophthalmology (Germany), 236/5 (1998), pp. 380-389.

Volchek and Dellen, "Anaphylaxis to Intravenous Cyclosporine and Tolerance to Oral Cyclosporine, Case Report and Review", Annals of Allergy, Asthma, and Immunology, 80 (1998), pp. 159-163.

Singla et al., "Paclitaxel and its Formulations", International Journal of Pharmaceutics, 235/1-2 (2002), pp. 179-192.

US 5,849,884, 12/1998, Woiszwillo et al. (withdrawn)

* cited by examiner

POLYMORPHIC FORM OF ITRACONAZOLE

CROSS-REFERENCE TO RELATED APPLICATION

This application is a continuation in part of application Ser. No. 10/035,821 filed Oct. 19, 2001, which is a continuation in part of application Ser. No. 09/953,979 filed Oct. 17, 2001 which is a continuation in part of application Ser. No. 09/874,637 filed on Jun. 5, 2001, now U.S. Pat. No. 6,869,617, which claims priority from provisional application Ser. No. 60/258,160 filed Dec. 22, 2000, each of which is incorporated herein by reference and made a part hereof.

FEDERALLY SPONSORED RESEARCH OR DEVELOPMENT

Not Applicable.

BACKGROUND OF THE INVENTION

1. Technical Field

The present invention relates to a polymorphic form of itraconazole.

2. Background Art

There is an ever increasing number of pharmaceutical drugs being formulated that are poorly soluble or insoluble in aqueous solutions. Such drugs provide challenges to delivering them in an injectable form such as through parenteral administration. Drugs that are insoluble in water can have significant benefits when formulated as a stable suspension of sub-micron particles. Accurate control of particle size is essential for safe and efficacious use of these formulations. Particles must be less than seven microns in diameter to safely pass through capillaries without causing emboli (Allen et al., 1987; Davis and Taube, 1978; Schroeder et al., 1978; Yokel et al., 1981).

One approach to delivering an insoluble drug is disclosed in U.S. Pat. No. 2,745,785. This patent discloses a method for preparing crystals of penicillin G suitable for parenteral administration. The method includes the step of recrystallizing the penicillin G from a formamide solution by adding water to reduce the solubility of the penicillin G. The '785 patent further provides that the penicillin G particles can be coated with wetting agents such as lecithin, or emulsifiers, surface-active and defoaming agents, or partial higher fatty acid esters of sorbitan or polyoxyalkyklene derivatives thereof, or aryl alkyl polyether alcohols or salts thereof. The '785 patent further discloses micronizing the penicillin G with an air blast under pressure to form crystals ranging from about 5 to 20 microns.

Another approach is disclosed in U.S. Pat. No. 5,118,528 which discloses a process for preparing nanoparticles. The process includes the steps of: (1) preparing a liquid phase of a substance in a solvent or a mixture of solvents to which may be added one or more surfactants, (2) preparing a second liquid phase of a non-solvent or a mixture of non-solvents, the non-solvent is miscible with the solvent or mixture of solvents for the substance, (3) adding together the solutions of (1) and (2) with stirring; and (4) removing of unwanted solvents to produce a colloidal suspension of nanoparticles. The '528 patent discloses that it produces particles of the substance smaller than 500 nm without the supply of energy. In particular the '528 patent states that it is undesirable to use high energy equipment such as sonicators and homogenizers.

U.S. Pat. No. 4,826,689 discloses a method for making uniformly sized particles from water-insoluble drugs or other organic compounds. First, a suitable solid organic compound is dissolved in an organic solvent, and the solution can be diluted with a non-solvent. Then, an aqueous precipitating liquid is infused, precipitating non-aggregated particles with substantially uniform mean diameter. The particles are then separated from the organic solvent. Depending on the organic compound and the desired particle size, the parameters of temperature, ratio of non-solvent to organic solvent, infusion rate, stir rate, and volume can be varied according to the invention. The '689 patent discloses this process forms a drug in a metastable state which is thermodynamically unstable and which eventually converts to a more stable crystalline state. The '689 patent discloses trapping the drug in a metastable state in which the free energy lies between that of the starting drug solution and the stable crystalline form. The '689 patent discloses utilizing crystallization inhibitors (e.g., polyvinylpyrrolidinone) and surface-active agents (e.g., poly(oxyethylene)-co-oxypropylene) to render the precipitate stable enough to be isolated by centrifugation, membrane filtration or reverse osmosis.

In U.S. Pat. Nos. 5,091,188; 5,091,187 and 4,725,442 which disclose (a) either coating small drug particles with natural or synthetic phospholipids or (b) dissolving the drug in a suitable lipophilic carrier and forming an emulsion stabilized with natural or semisynthetic phospholipids. One of the disadvantages of these approaches is they rely on the quality of the raw material of the drug and do not disclose steps of changing the morphology of the raw material to render the material in a friable, more easily processed form.

Another approach to providing insoluble drugs for parenteral delivery is disclosed in U.S. Pat. No. 5,145,684. The '684 patent discloses the wet milling of an insoluble drug in the presence of a surface modifier to provide a drug particle having an average effective particle size of less than 400 nm. The '684 patent emphasizes the desirability of not using any solvents in its process. The '684 patent discloses the surface modifier is adsorbed on the surface of the drug particle in an amount sufficient to prevent agglomeration into larger particles.

Yet another attempt to provide insoluble drugs for parenteral delivery is disclosed in U.S. Pat. No. 5,922,355. The '355 patent discloses providing submicron sized particles of insoluble drugs using a combination of surface modifiers and a phospholipid followed by particle size reduction using techniques such as sonication, homogenization, milling, microfluidization, precipitation or recrystallization. There is no disclosure in the '355 patent of changing process conditions to make crystals in a more friable form.

U.S. Pat. No. 5,780,062 discloses a method of preparing small particles of insoluble drugs by (1) dissolving the drug in a water-miscible first solvent, (2) preparing a second solution of a polymer and an amphiphile in an aqueous second solvent in which the drug is substantially insoluble whereby a polymer/amphiphile complex is formed; and (3) mixing the solutions from the first and second steps to precipitate an aggregate of the drug and polymer/amphiphile complex.

U.S. Pat. No. 5,858,410 discloses a pharmaceutical nanosuspension suitable for parenteral administration. The '410 patent discloses subjecting at least one solid therapeutically active compound dispersed in a solvent to high pressure homogenization in a piston-gap homogenizer to form particles having an average diameter, determined by photon correlation spectroscopy (PCS) of 10 nm to 1000 nm, the proportion of particles larger than 5 μm in the total population being less than 0.1% (number distribution determined with a Coulter counter), without prior conversion into a melt, wherein the active compound is solid at room temperature and is insoluble, only sparingly soluble or moderately soluble in water, aqueous media and/or organic solvents. The Examples in the '410 patent disclose jet milling prior to homogenization.

U.S. Pat. No. 4,997,454 discloses a method for making uniformly sized particles from solid compounds. The method of the '454 patent includes the steps of dissolving the solid compound in a suitable solvent followed by infusing precipitating liquid thereby precipitating non-aggregated particles with substantially uniform mean diameter. The particles are then separated from the solvent. The '454 patent discourages forming particles in a crystalline state because during the precipitating procedure the crystal can dissolve and recrystallize thereby broadening the particle size distribution range. The '454 patent encourages during the precipitating procedure to trap the particles in a metastable particle state.

U.S. Pat. No. 5,605,785 discloses a process for forming nanoamorphous dispersions of photographically useful compounds. The process of forming nanoamorphous dispersions include any known process of emulsification that produces a disperse phase having amorphous particulates.

U.S. Pat. No. 6,346,533 discloses an amorphous form of itraconazole exhibiting an improved solubility. The amorphous form disclosed in the '533 patent is prepared by dissolving itraconazole in an organic solvent followed by dissolution-induced drying the mixture with a spray dryer, fluid-bed granulator, or a centrifugal granulator. The amorphous particles formed by this process have a particle diameter of 0.5 to 10 μm and exhibit an improved bioavailability.

SUMMARY OF THE INVENTION

The present invention provides a polymorphic form of itraconazole having an X-ray diffractogram substantially as shown in FIG. 12b, characterized by peaks in the powder X-ray diffraction at values in degrees of two theta of approximately 7.3 degrees, 19.9 degrees, 21.9 degrees, 26.1 degrees, and 32.2 degrees. The polymorphic form of itraconzaole is further characterized by having a Fourier transform infrared (FTIR) spectrum substantially the same as that shown in FIG. 18b. The polymorphic form of itraconazole is even further characterized by having a DSC profile substantially the same as shown in FIG. 13b.

These and other aspects and attributes of the present invention will be discussed with reference to the following drawings and accompanying specification.

DETAILED DESCRIPTION OF THE INVENTION

Figure 1:
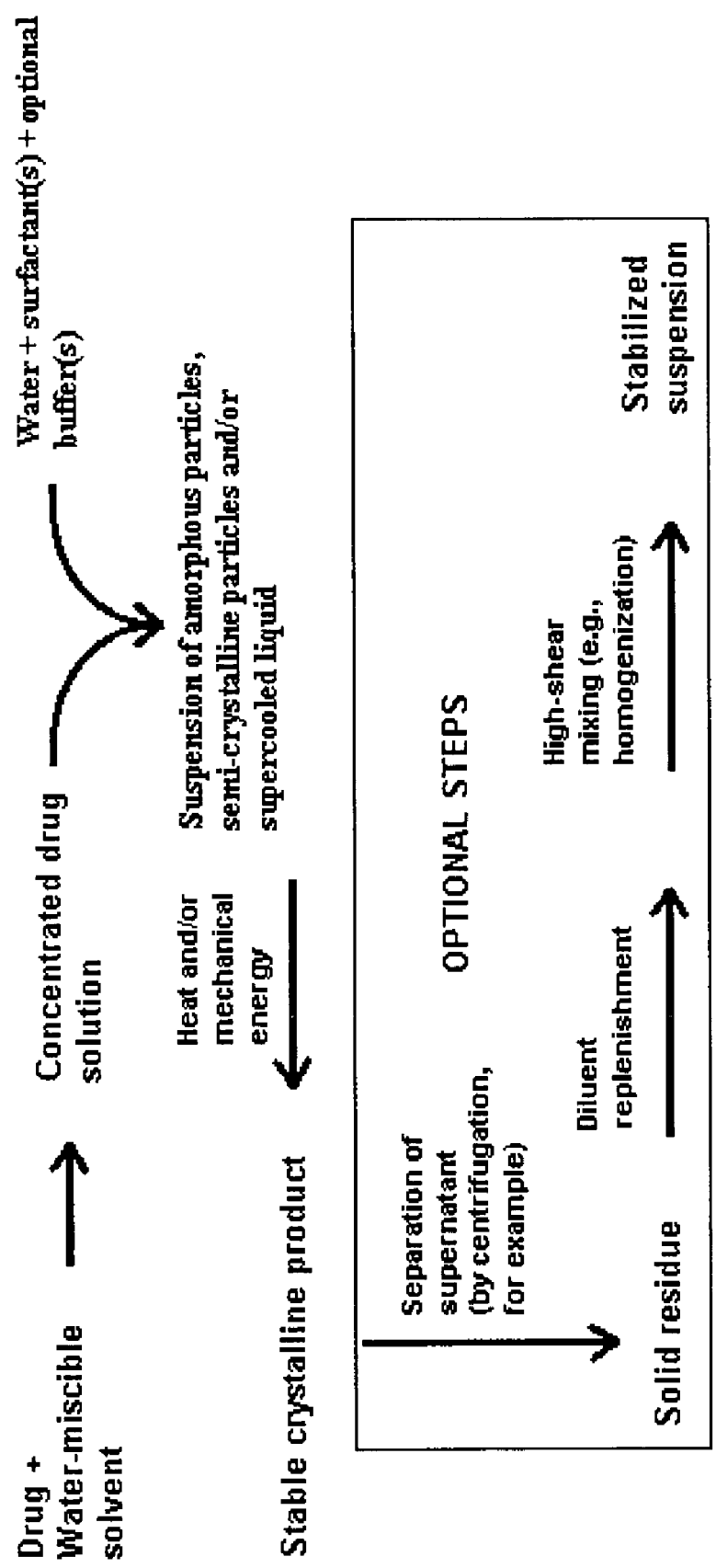
FIG. 1 shows a diagrammatic representation of one method of the present invention.

The present invention is susceptible of embodiments in many different forms. Preferred embodiments of the invention are disclosed with the understanding that the present disclosure is to be considered as exemplifications of the principles of the invention and are not intended to limit the broad aspects of the invention to the embodiments illustrated.

The present invention provides methods or processes for forming particles of an organic compound having an average effective particle size suitable for parenteral administration and, in a most preferred form of the invention, is less than about 2 μm.

The processes can be separated into three general categories. Each of the categories of processes share the steps of: (1) dissolving an organic compound in a water miscible first organic solvent to create a first solution, (2) mixing the first solution with a second solvent of water to precipitate the organic compound to create a pre-suspension, and (3) adding energy to the pre-suspension in the form of high-shear mixing or heat to provide a stable form of the organic compound having the desired size ranges defined above.

The three categories of processes are distinguished based upon the physical properties of the organic compound as determined through X-ray diffraction studies, differential scanning calorimetry (DSC) studies or other suitable study conducted prior to the energy-addition step and after the energy-addition step. In the first process category, prior to the energy-addition step the organic compound in the pre-suspension takes an amorphous form, a semi-crystalline form or a supercooled liquid form and has an average effective particle size. After the energy-addition step the organic compound is in a crystalline form having an average effective particle size essentially the same as that of the pre-suspension (i.e., from less than about 2 µm).

In the second process category, prior to the energy-addition step the organic compound is in a crystalline form and has an average effective particle size. After the energy-addition step the organic compound is in a crystalline form having essentially the same average effective particle size as prior to the energy-addition step but the crystals after the energy-addition step are less likely to aggregate.

The lower tendency of the organic compound to aggregate is observed by laser dynamic light scattering and light microscopy.

In the third process category, prior to the energy-addition step the organic compound is in a crystalline form that is friable and has an average effective particle size. What is meant by the term "friable" is that the particles are fragile and are more easily broken down into smaller particles. After the energy-addition step the organic compound is in a crystalline form having an average effective particle size smaller than the crystals of the pre-suspension. By taking the steps necessary to place the organic compound in a crystalline form that is friable, the subsequent energy-addition step can be carried out more quickly and efficiently when compared to an organic compound in a less friable crystalline morphology.

The energy-addition step can be carried out in any fashion wherein the pre-suspension is exposed to cavitation, shearing or impact forces. In one preferred form of the invention, the energy-addition step is an annealing step. Annealing is defined in this invention as the process of converting matter that is thermodynamically unstable into a more stable form by single or repeated application of energy (direct heat or mechanical stress), followed by thermal relaxation. This lowering of energy may be achieved by conversion of the solid form from a less ordered to a more ordered lattice structure. Alternatively, this stabilization may occur by a reordering of the surfactant molecules at the solid-liquid interface.

These three process categories will be discussed separately below. It should be understood, however, that the process conditions such as choice of surfactants or combination of surfactants, amount of surfactant used, temperature of reaction, rate of mixing of solutions, rate of precipitation and the like can be selected to allow for any drug to be processed under any one of the categories discussed next.

Figure 2:
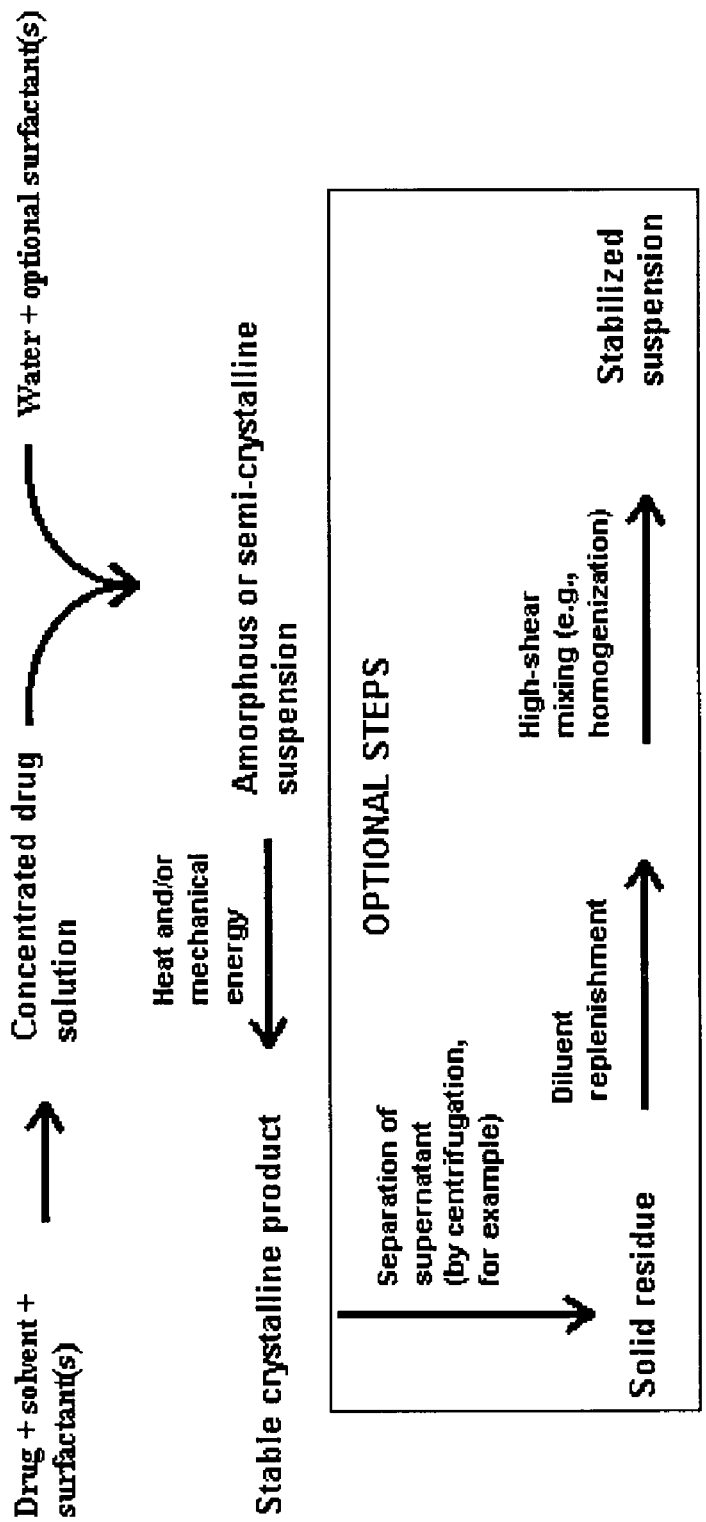
FIG. 2 show a diagrammatic representation of another method of the present invention.

The first process category, as well as the second and third process categories, can be further divided into two subcategories, Method A, and B shown in FIGS. 1 and 2 respectively.

An organic compound for use in the process of this invention is any organic chemical entity whose solubility decreases from one solvent to another. This organic compound might be a pharmaceutically active compound from various groups such as, but not limited to: antihyperlipidemics; antimicrobials, e.g., antibacterials such as sulfadiazine, antifungals such as itraconazole; non-steroidal anti-inflammatory drugs, e.g., indomethacin; antihypercholesteremic agents, e.g., probucol; and steroidal compounds, e.g., dexamethasone; immunosuppresants, e.g., cyclosporin A, tacrolimus, and mycophenolate mofetil. Or the organic compound might be from the group used as adjuvants or excipients in pharmaceutical preparations and cosmetics, such as, but not limited to, preservatives, e.g., propylparaben.

The first solvent according to the present invention is a solvent or mixture of solvents in which the organic compound of interest is relatively soluble and which is miscible with the second solvent. Examples of such solvents include, but are not limited to: polyvinylpyrrolidone, N-methyl-2-pyrrolidinone (also called N-methyl-2-pyrrolidone), 2-pyrrolidone, dimethyl sulfoxide, dimethylacetamide, lactic acid, methanol, ethanol, isopropanol, 3-pentanol, n-propanol, glycerol, butylene glycol (butanediol), ethylene glycol, propylene glycol, mono- and diacylated monoglycerides (such as glyceryl caprylate), dimethyl isosorbide, acetone, dimethylformamide, 1,4-dioxane, polyethylene glycol (for example, PEG-4, PEG-8, PEG-9, PEG-12, PEG-14, PEG-16, PEG-120, PEG-75, PEG-150, polyethylene glycol esters (examples such as PEG-4 dilaurate, PEG-20 dilaurate, PEG-6 isostearate, PEG-8 palmitostearate, PEG-150 palmitostearate), polyethylene glycol sorbitans (such as PEG-20 sorbitan isostearate), polyethylene glycol monoalkyl ethers (examples such as PEG-3 dimethyl ether, PEG-4 dimethyl ether), polypropylene glycol (PPG), polypropylene alginate, PPG-10 butanediol, PPG-10 methyl glucose ether, PPG-20 methyl glucose ether, PPG-15 stearyl ether, propylene glycol dicaprylate/dicaprate, propylene glycol laurate.

Method A

In Method A (see FIG. 1), the organic compound ("drug") is first dissolved in the first solvent to create a first solution. The organic compound can be added from about 0.1% (w/v) to about 50% (w/v) depending on the solubility of the organic compound in the first solvent. Heating of the concentrate from about 30° C. to about 100° C. may be necessary to ensure total dissolution of the compound in the first solvent.

A second aqueous solution is provided with one or more optional surface modifiers such as an anionic surfactant, a cationic surfactant, a nonionic surfactant or a biological surface active molecule added thereto. Suitable anionic surfactants include but are not limited to potassium laurate, sodium lauryl sulfate, sodium dodecylsulfate, alkyl polyoxyethylene sulfates, sodium alginate, dioctyl sodium sulfosuccinate, phosphatidyl choline, phosphatidyl glycerol, phosphatidyl inosine, phosphatidylserine, phosphatidic acid and their salts, glyceryl esters, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate, etc.). Suitable cationic surfactants include but are not limited to quaternary ammonium compounds, such as benzalkonium chloride, cetyltrimethylammonium bromide, lauryldimethylbenzylammonium chloride, acyl carnitine hydrochlorides, or alkyl pyridinium halides. As anionic surfactants, phospholipids may be used. Suitable phospholipids include, for example phosphatidylcholine, phosphatidylethanolamine, phosphatidylserine, phosphatidylinositol, phosphatidylglycerol, phosphatidic acid, lysophospholipids, egg or soybean phospholipid or a combination thereof. The phospholipid may be salted or desalted, hydrogenated or partially hydrogenated or natural semisynthetic or synthetic.

Suitable nonionic surfactants include: polyoxyethylene fatty alcohol ethers (Macrogol and Brij), polyoxyethylene sorbitan fatty acid esters (Polysorbates), polyoxyethylene fatty acid esters (Myij), sorbitan esters (Span), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxomers), polaxamines, methylcellulose, hydroxycellulose, hydroxy propylcellulose, hydroxy propylmethylcellulose, noncrystalline cellulose, polysaccharides including starch and starch derivatives such as hydroxyethylstarch (HES), polyvinyl alcohol, and polyvinylpyrrolidone. In a preferred form of the invention the nonionic surfactant is a polyoxyethylene and polyoxypropylene copolymer and preferably a block copolymer of propylene glycol and ethylene glycol. Such polymers are sold under the tradename POLOXAMER also sometimes referred to as PLURONIC®, and sold by several suppliers including Spectrum Chemical and Ruger. Among polyoxyethylene fatty acid esters is included those having short alkyl chains. One example of such a surfactant is SOLUTOL® HS 15, polyethylene-660-hydroxystearate, manufactured by BASF Aktiengesellschaft.

Surface active biological molecules include such molecules as albumin, casein, heparin, hirudin or other appropriate proteins.

It may also be desirable to add a pH adjusting agent to the second solution such as sodium hydroxide, hydrochloric acid, tris buffer or citrate, acetate, lactate, meglumine, or the like. The second solution should have a pH within the range of from about 3 to about 11.

In a preferred form of the invention, the method for preparing submicron sized particles of an organic compound includes the steps of adding the first solution to the second solution. The addition rate is dependent on the batch size, and precipitation kinetics for the organic compound. Typically, for a small-scale laboratory process (preparation of 1 liter), the addition rate is from about 0.05 cc per minute to about 10 cc per minute. During the addition, the solutions should be under constant agitation. It has been observed using light microscopy that amorphous particles, semicrystalline solids, or a supercooled liquid are formed to create a pre-suspension. The method further includes the step of subjecting the pre-suspension to an annealing step to convert the amorphous particles, supercooled liquid or semicrystalline solid to a crystalline more stable solid state. The resulting particles will have an average effective particles size as measured by dynamic light scattering methods (e.g., photocorrelation spectroscopy, laser diffraction, low-angle laser light scattering (LALLS), medium-angle laser light scattering (MALLS), light obscuration methods (Coulter method, for example), rheology, or microscopy (light or electron) within the ranges set forth above).

The energy-addition step involves adding energy through sonication, homogenization, counter current flow homogenization, microfluidization, or other methods of providing impact, shear or cavitation forces. The sample may be cooled or heated during this stage. In one preferred form of the invention the annealing step is effected by a piston gap homogenizer such as the one sold by Avestin Inc. under the product designation EmulsiFlex-C160. In another preferred form of the invention the annealing may be accomplished by ultrasonication using an ultrasonic processor such as the Vibra-Cell Ultrasonic Processor (600W), manufactured by Sonics and Materials, Inc. In yet another preferred form of the invention the annealing may be accomplished by use of an emulsification apparatus as described in U.S. Pat. No. 5,720,551 which is incorporated herein by reference and made a part hereof.

Depending upon the rate of annealing, it may be desirable to adjust the temperature of the processed sample to within the range of from approximately −30° C. to 30° C. Alternatively, in order to effect a desired phase change in the processed solid, it may also be necessary to heat the presuspension to a temperature within the range of from about 30° C. to about 100° C. during the annealing step.

Method B

Method B differs from Method A in the following respects. The first difference is a surfactant or combination of surfactants is added to the first solution. The surfactants may be selected from the groups of anionic, nonionic and cationic surfactants set forth above.

Comparative Example of Method A and Method B and U.S. Pat. No. 5,780,062

U.S. Pat. No. 5,780,062 discloses a process for preparing small particles of an organic compound by first dissolving the compound in a suitable water-miscible first solvent. A second solution is prepared by dissolving a polymer and an amphiphile in aqueous solution. The first solution is then added to the second solution to form a precipitate that consists of the organic compound and a polymer-amphiphile complex. The '062 patent does not disclose utilizing the energy-addition step of this invention in Methods A and B. Lack of stability is typically evidenced by rapid aggregation and particle growth. In some instances, amorphous particles recrystallize as large crystals. Adding energy to the pre-suspension in the manner disclosed above typically affords particles that show decreased rates of particle aggregation and growth, as well as the absence of recrystallization upon product storage.

Methods A and B are further distinguished from the process of the '062 patent by the absence of a step of forming a polymer-amphiphile complex prior to precipitation. In Method A, such a complex cannot be formed as no polymer is added to the diluent (aqueous) phase. In Method B, the surfactant, which may also act as an amphiphile, or polymer, is dissolved with the organic compound in the first solvent. This precludes the formation of any amphiphile-polymer complexes prior to precipitation. In the '062 patent, successful precipitation of small particles relies upon the formation of an amphiphile-polymer complex prior to precipitation. The '062 patent discloses the amphiphile-polymer complex forms aggregates in the aqueous second solution. The '062 patent explains the hydrophobic organic compound interacts with the amphiphile-polymer complex, thereby reducing solubility of these aggregates and causing precipitation. In the present invention it has been demonstrated that the inclusion of the surfactant or polymer in the first solvent (Method B) leads, upon subsequent addition to second solvent, to formation of a more uniform, finer particulate than is afforded by the process outlined by the '062 patent.

To this end, two formulations were prepared and analyzed. Each of the formulations have two solutions, a concentrate and an aqueous diluent, which are mixed together and then sonicated. The concentrate in each formulation has an organic compound (itraconazole), a water miscible solvent (N-methyl-2-pyrrolidinone or NMP) and possibly a polymer (poloxamer 188). The aqueous diluent has water, a tris buffer and possibly a polymer (poloxamer 188) and/or a surfactant (sodium deoxycholate). The average particle diameter of the organic particle is measured prior to sonication and after sonication.

The first formulation A has as the concentrate itraconazole and NMP. The aqueous diluent includes water, poloxamer 188, tris buffer and sodium deoxycholate. Thus the aqueous diluent includes a polymer (poloxamer 188), and an amphiphile (sodium deoxycholate), which may form a polymer/amphiphile complex, and, therefore, is in accordance with the disclosure of the '062 patent. (However, again the '062 patent does not disclose an energy addition step.)

The second formulation B has as the concentrate itraconazole, NMP and poloxamer 188. The aqueous diluent includes water, tris buffer and sodium deoxycholate. This formulation is made in accordance with the present invention. Since the aqueous diluent does not contain a combination of a polymer (poloxamer) and an amphiphile (sodium deoxycholate), a polymer/amphiphile complex cannot form prior to the mixing step.

Table 1 shows the average particle diameters measured by laser diffraction on three replicate suspension preparations. An initial size determination was made, after which the sample was sonicated for 1 minute. The size determination was then repeated. The large size reduction upon sonication of Method A was indicative of particle aggregation.

Furthermore, any undesired excipients such as surfactants may be replaced by a more desirable excipient by use of the separation methods described in the above paragraph. The solvent and first excipient may be discarded with the supernatant after centrifugation or filtration. A fresh volume of the suspension vehicle without the solvent and without the first excipient may then be added. Alternatively, a new surfactant may be added. For example, a suspension consisting of drug, N-methyl-2-pyrrolidinone (solvent), poloxamer 188 (first excipient), sodium deoxycholate, glycerol and water may be replaced with phospholipids (new surfactant), glycerol and water after centrifugation and removal of the supernatant.

I. First Process Category

The methods of the first process category generally include the step of dissolving the organic compound in a water miscible first solvent followed by the step of mixing this solution with an aqueous solution to form a pre-suspension wherein the organic compound is in an amorphous form, a semicrystalline form or in a supercooled liquid form as determined by X-ray diffraction studies, DSC, light microscopy or other analytical techniques and has an average effective particle size within one of the effective particle size ranges set forth above. The mixing step is

TABLE 1

| Method | Concentrate | Aqueous Diluent | Average particle diameter (microns) | After sonication (1 minute) |
|---|---|---|---|---|
| A | itraconazole (18%), N-methyl-2-pyrrolidinone (6 mL) | poloxamer 188 (2.3%), sodium deoxycholate (0.3%)tris buffer (5 mM, pH 8)water (qs to 94 mL) | 18.7<br>10.7<br>12.1 | 2.36<br>2.46<br>1.93 |
| B | itraconazole (18%)poloxamer 188 (37%)N-methyl-2-pyrrolidinone (6 mL) | sodium deoxycholate (0.3%)tris buffer (5 mM, pH 8)water (qs to 94 mL) | 0.194<br>0.178<br>0.181 | 0.198<br>0.179<br>0.177 |

A drug suspension resulting from application of the processes described in this invention may be administered directly as an injectable solution, provided Water for Injection is used in formulation and an appropriate means for solution sterilization is applied. Sterilization may be accomplished by separate sterilization of the drug concentrate (drug, solvent, and optional surfactant) and the diluent medium (water, and optional buffers and surfactants) prior to mixing to form the pre-suspension. Sterilization methods would include pre-filtration first through a 3.0 micron filter followed by filtration through a 0.45-micron particle filter, followed by steam or heat sterilization or sterile filtration through two redundant 0.2-micron membrane filters.

Optionally, a solvent-free suspension may be produced by solvent removal after precipitation. This can be accomplished by centrifugation, dialysis, diafiltration, force-field fractionation, high-pressure filtration or other separation techniques well known in the art. Complete removal of N-methyl-2-pyrrolidinone was typically carried out by one to three successive centrifugation runs; after each centrifugation (18,000 rpm for 30 minutes) the supernatant was decanted and discarded. A fresh volume of the suspension vehicle without the organic solvent was added to the remaining solids and the mixture was dispersed by homogenization. It will be recognized by others skilled in the art that other high-shear mixing techniques could be applied in this reconstitution step.

followed by an energy-addition step and, in a preferred form of the invention an annealing step.

II. Second Process Category

The methods of the second processes category include essentially the same steps as in the steps of the first processes category but differ in the following respect. An X-ray diffraction, DSC or other suitable analytical techniques of the pre-suspension shows the organic compound in a crystalline form and having an average effective particle size. The organic compound after the energy-addition step has essentially the same average effective particle size as prior to the energy-addition step but has less of a tendency to aggregate into larger particles when compared to that of the particles of the pre-suspension. Without being bound to a theory, it is believed the differences in the particle stability may be due to a reordering of the surfactant molecules at the solid-liquid interface.

III. Third Process Category

The methods of the third category modify the first two steps of those of the first and second processes categories to ensure the organic compound in the pre-suspension is in a friable form having an average effective particle size (e.g., such as slender needles and thin plates). Friable particles can be formed by selecting suitable solvents, surfactants or combination of surfactants, the temperature of the individual solutions, the rate of mixing and rate of precipitation and the like. Friability may also be enhanced by the introduction of lattice defects (e.g., cleavage planes) during the steps of mixing the first solution with the aqueous solution. This would arise by rapid crystallization such as that afforded in the precipitation step. In the energy-addition step these friable crystals are converted to crystals that are kinetically stabilized and having an average effective particle size smaller than those of the pre-suspension. Kinetically stabilized means particles have a reduced tendency to aggregate when compared to particles that are not kinetically stabilized. In such instance the energy-addition step results in a breaking up of the friable particles. By ensuring the particles of the pre-suspension are in a friable state, the organic compound can more easily and more quickly be prepared into a particle within the desired size ranges when compared to processing an organic compound where the steps have not been taken to render it in a friable form.

Polymorph Control

The present invention further provides additional steps for controlling the crystal structure of the pharmaceutically-active compound to ultimately produce a suspension of the compound in the desired size range and a desired crystal structure. What is meant by the term "crystal structure" is the arrangement and/or conformation of the molecules within the crystal lattice. Compounds that can be crystallized into different crystal structures are said to be polymorphic. Identification of polymorphs is important step in drug formulation since different polymorphs of the same drug can show differences in solubility, therapeutic activity, bioavailabilty, and suspension stability. Accordingly, it is important to control the polymorphic form of the compound for ensuring product purity and batch-to-batch reproducibility.

The steps to control the polymorphic form of the compound includes seeding the first solution, the second solvent or the pre-suspension to ensure the formation of the desired polymorph. Seeding includes using a seed compound or adding energy to form the seed compound. In a preferred form of the invention the seed compound is the pharmaceutically-active compound in the desired polymorphic form. Alternatively, the seed compound can also be an inert impurity or an organic compound with a structure similar to that of the desired polymorph such as a bile salt.

The seed compound can be precipitated from the first solution. This method includes the steps of adding the pharmaceutically-active compound in sufficient quantity to exceed the solubility of the pharmaceutically-active compound in the first solvent to create a supersaturated solution. The supersaturated solution is treated to precipitate the pharmaceutically-active compound in the desired polymorphic form. Treating the supersaturated solution includes aging the solution for a time period until the formation of a crystal or crystals is observed to create a seeding mixture. It is also possible to add energy to the supersaturated solution to cause the pharmaceutically-active compound to precipitate out of the solution in the desired polymorph. The energy can be added in a variety of ways including the energy addition steps described above. Further energy can be added by heating or exposing the pre-suspension to electromagnetic energy, particle beam or electron beam sources. The electromagnetic energy includes using a laser beam, dynamic electromagnetic energy, or other radiation sources It is further contemplated utilizing ultrasound, static electric field and a static magnetic field as the energy addition source.

In a preferred form of the invention the method for producing seed crystals from an aged supersaturated solution includes the steps of: (i) adding a quantity of the pharmaceutically-active compound to the first organic solvent to create a supersaturated solution, (ii) aging the supersaturated solution to form detectable crystals to create a seeding mixture; and (iii) mixing the seeding mixture with the second solvent to precipitate the pharmaceutically-active compound to create a pre-suspension. The pre-suspension can then be further processed as described in detail above to provide an aqueous suspension of the pharmaceutically-active compound in the desired polymorph and in the desired size range.

Seeding can also be accomplished by adding energy to the first solution, the second solvent or the pre-suspension provided that the exposed liquid or liquids contain the pharmaceutically active compound or a seed material. The energy can be added in the same fashion as described above for the supersaturated solution.

Accordingly, the present invention provides a composition of matter of a pharmaceutically active compound in a desired polymorphic form essentially free of the unspecified polymorph or polymorphs. One such example is set forth in example 16 below where seeding during microprecipitation provides a polymorph of itraconazole essentially free of the polymorph of the raw material. It is contemplated the methods of this invention can apply used to selectively produce a desired polymorph for numerous pharmaceutically active compounds.

EXAMPLES

Examples of Process Category 1

Example 1

Preparation of Itraconazole Suspension by Use of Process Category 1, Method A with Homogenization To a 3-L flask add 1680 mL of Water for Injection. Heat liquid to 60–65° C., and then slowly add 44 grams of Pluronic F-68 (poloxamer 188), and 12 grams of sodium deoxycholate, stirring after each addition to dissolve the solids. After addition of solids is complete, stir for another 15 minutes at 60–65° C. to ensure complete dissolution. Prepare a 50 mM tris (tromethamine) buffer by dissolving 6.06 grams of tris in 800 mL of Water for Injection. Titrate this solution to pH 8.0 with 0.1 M hydrochloric acid. Dilute the resulting solution to 1 liter with additional Water for Injection. Add 200 mL of the tris buffer to the poloxamer/deoxycholate solution. Stir thoroughly to mix solutions.

In a 150-mL beaker add 20 grams of itraconazole and 120 mL of N-methyl-2-pyrrolidinone. Heat mixture to 50–60° C., and stir to dissolve solids. After total dissolution is visually apparent, stir another 15 minutes to ensure complete dissolution. Cool itraconazole-NMP solution to room temperature.

Figure 3:
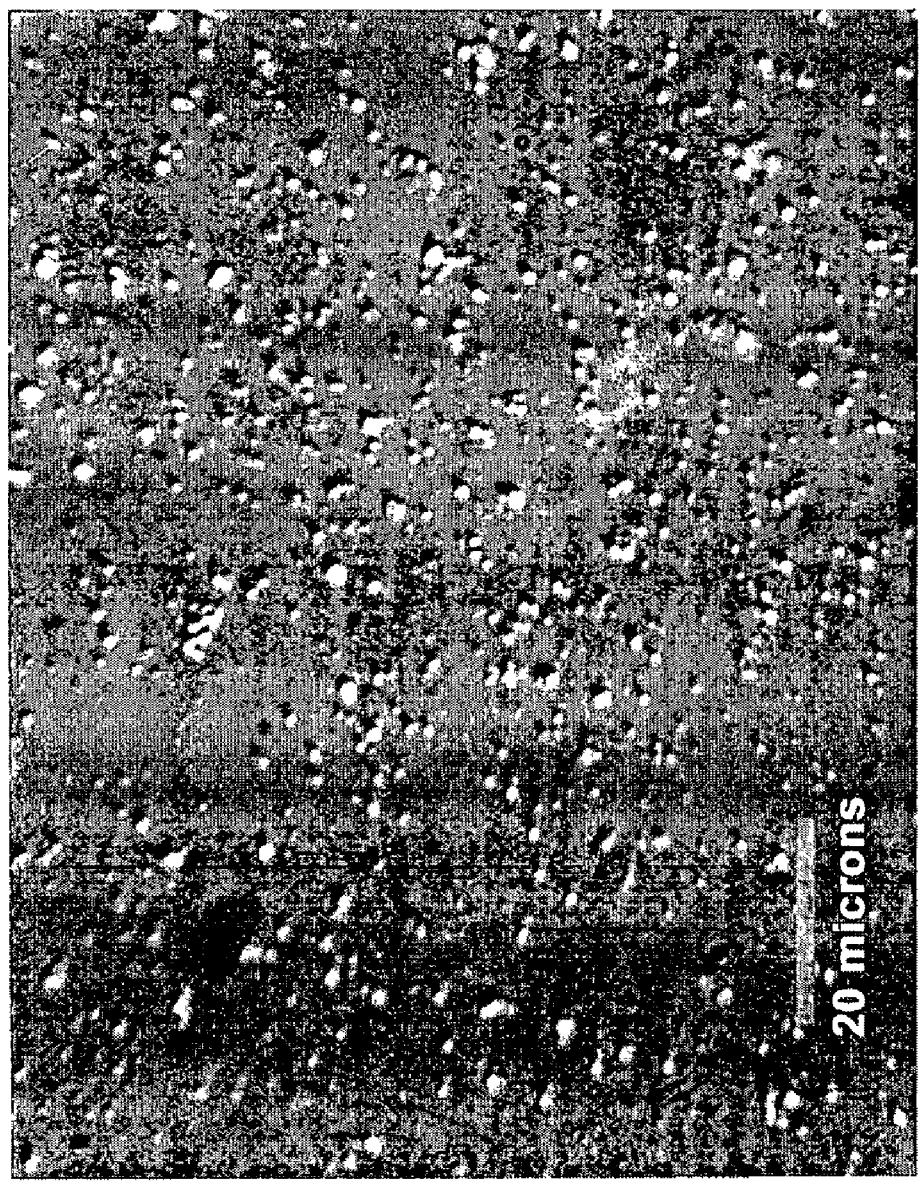
FIG. 3 shows amorphous particles prior to homogenization.

Charge a syringe pump (two 60-mL glass syringes) with the 120-mL of itraconazole solution prepared previously. Meanwhile pour all of the surfactant solution into a homogenizer hopper which has been cooled to 0–5° C. (this may either by accomplished by use of a jacketed hopper through which refrigerant is circulated, or by surrounding the hopper with ice). Position a mechanical stirrer into the surfactant solution so that the blades are fully immersed. Using the syringe pump, slowly (1–3 mL/min) add all of the itraconazole solution to the stirred, cooled surfactant solution. A stirring rate of at least 700 rpm is recommended. An aliquot of the resulting suspension (Suspension A) is analyzed by light microscopy (Hoffman Modulation Contrast) and by laser diffraction (Horiba). Suspension A is observed by light microscopy to consist of roughly spherical amorphous particles (under 1 micron), either bound to each other in aggregates or freely moving by Brownian motion. See FIG. 3. Dynamic light scattering measurements typically afford a bimodal distribution pattern signifying the presence of aggregates (10–100 microns in size) and the presence of single amorphous particles ranging 200–700 nm in median particle diameter.

Figure 4:
FIG. 4 shows particles after annealing by homogenization.

The suspension is immediately homogenized (at 10,000 to 30,000 psi) for 10–30 minutes. At the end of homogenization, the temperature of the suspension in the hopper does not exceed 75° C. The homogenized suspension is collected in 500-mL bottles, which are cooled immediately in the refrigerator (2–8° C.). This suspension (Suspension B) is analyzed by light microscopy and is found to consist of small elongated plates with a length of 0.5 to 2 microns and a width in the 0.2–1 micron range. See FIG. 4. Dynamic light scattering measurements typically indicate a median diameter of 200–700 nm.

Stability of Suspension A ("Pre-suspension")

Example 1

During microscopic examination of the aliquot of Suspension A, crystallization of the amorphous solid was directly observed. Suspension A was stored at 2–8° C. for 12 hours and examined by light microscopy. Gross visual inspection of the sample revealed severe flocculation, with some of the contents settling to the bottom of the container. Microscopic examination indicated the presence of large, elongated, plate-like crystals over 10 microns in length.

Stability of Suspension B

As opposed to the instability of Suspension A, Suspension B was stable at 2–8° C. for the duration of the preliminary stability study (1 month). Microscopy on the aged sample clearly demonstrated that no significant change in the morphology or size of the particles had occurred. This was confirmed by light scattering measurement.

Example 2

Preparation of Itraconazole Suspension by Use of Process Category 1, Method A with Ultrasonication To a 500-mL stainless steel vessel add 252 mL of Water for Injection. Heat liquid to 60–65° C., and then slowly add 6.6 grams of Pluronic F-68 (poloxamer 188), and 0.9 grams of sodium deoxycholate, stirring after each addition to dissolve the solids. After addition of solids is complete, stir for another 15 minutes at 60–65° C. to ensure complete dissolution. Prepare a 50 mM tris (tromethamine) buffer by dissolving 6.06 grams of tris in 800 mL of Water for Injection. Titrate this solution to pH 8.0 with 0.1 M hydrochloric acid. Dilute the resulting solution to 1 liter with additional Water for Injection. Add 30 mL of the tris buffer to the poloxamer/deoxycholate solution. Stir thoroughly to mix solutions.

In a 30-mL container add 3 grams of itraconazole and 18 mL of N-methyl-2-pyrrolidinone. Heat mixture to 50–60° C., and stir to dissolve solids. After total dissolution is visually apparent, stir another 15 minutes to ensure complete dissolution. Cool itraconazole-NMP solution to room temperature.

Charge a syringe pump with 18-mL of itraconazole solution prepared in a previous step. Position a mechanical stirrer into the surfactant solution so that the blades are fully immersed. Cool the container to 0–5° C. by immersion in an ice bath. Using the syringe pump, slowly (1–3 mL/min) add all of the itraconazole solution to the stirred, cooled surfactant solution. A stirring rate of at least 700 rpm is recommended. Immerse an ultrasonicator horn in the resulting suspension so that the probe is approximately 1 cm above the bottom of the stainless steel vessel. Sonicate (10,000 to 25,000 Hz, at least 400W) for 15 to 20 minute in 5-minute intervals. After the first 5-minute sonication, remove the ice bath and proceed with further sonication. At the end of ultrasonication, the temperature of the suspension in the vessel does not exceed 75° C.

The suspension is collected in a 500-mL Type I glass bottle, which is cooled immediately in the refrigerator (2–8° C.). Characteristics of particle morphology of the suspension before and after sonication were very similar to that seen in Method A before and after homogenization (see Example 1).

Example 3

Preparation of Itraconazole Suspension by Use of Process Category 1, Method B with Homogenization Prepare a 50 mM tris (tromethamine) buffer by dissolving 6.06 grams of tris in 800 mL of Water for Injection. Titrate this solution to pH 8.0 with 0.1 M hydrochloric acid. Dilute the resulting solution to 1 liter with additional Water for Injection. To a 3-L flask add 1680 mL of Water for Injection. Add 200 mL of the tris buffer to the 1680 mL of water. Stir thoroughly to mix solutions.

In a 150-mL beaker add 44 grams of Pluronic F-68 (poloxamer 188) and 12 grams of sodium deoxycholate to 120 mL of N-methyl-2-pyrrolidinone. Heat the mixture to 50–60° C., and stir to dissolve solids. After total dissolution is visually apparent, stir another 15 minutes to ensure complete dissolution. To this solution, add 20 grams of itraconazole, and stir until totally dissolved. Cool the itraconazole-surfactant-NMP solution to room temperature.

Charge a syringe pump (two 60-mL glass syringes) with the 120-mL of the concentrated itraconazole solution prepared previously. Meanwhile pour the diluted tris buffer solution prepared above into a homogenizer hopper which has been cooled to 0–5° C. (this may either by accomplished by use of a jacketed hopper through which refrigerant is circulated, or by surrounding the hopper with ice). Position a mechanical stirrer into the buffer solution so that the blades are fully immersed. Using the syringe pump, slowly (1–3 mL/min) add all of the itraconazole-surfactant concentrate to the stirred, cooled buffer solution. A stirring rate of at least 700 rpm is recommended. The resulting cooled suspension is immediately homogenized (at 10,000 to 30,000 psi) for 10–30 minutes. At the end of homogenization, the temperature of the suspension in the hopper does not exceed 75° C.

The homogenized suspension is collected in 500-mL bottles, which are cooled immediately in the refrigerator (2–8° C.). Characteristics of particle morphology of the suspension before and after homogenization were very similar to that seen in Example 1, except that in process category 1 B, the pre-homogenized material tended to form fewer and smaller aggregates which resulted in a much smaller overall particle size as measured by laser diffraction. After homogenization, dynamic light scattering results were typically identical to those presented in Example 1.

Example 4

Preparation of Itraconazole Suspension by Use of Process Category 1, Method B with Ultrasonication

To a 500-mL flask add 252 mL of Water for Injection. Prepare a 50 mM tris (tromethamine) buffer by dissolving 6.06 grams of tris in 800 mL of Water for Injection. Titrate this solution to pH 8.0 with 0.1 M hydrochloric acid. Dilute the resulting solution to 1 liter with additional Water for Injection. Add 30 mL of the tris buffer to the water. Stir thoroughly to mix solutions.

In a 30-mL beaker add 6.6 grams of Pluronic F-68 (poloxamer 188) and 0.9 grams of sodium deoxycholate to 18 mL of N-methyl-2-pyrrolidinone. Heat the mixture to 50–60° C., and stir to dissolve solids. After total dissolution is visually apparent, stir another 15 minutes to ensure complete dissolution. To this solution, add 3.0 grams of itraconazole, and stir until totally dissolved. Cool the itraconazole-surfactant-NMP solution to room temperature.

Charge a syringe pump (one 30-mL glass syringe with the 18-mL of the concentrated itraconazole solution prepared previously. Position a mechanical stirrer into the buffer solution so that the blades are fully immersed. Cool the container to 0–5° C. by immersion in an ice bath. Using the syringe pump, slowly (1–3 mL/min) add all of the itraconazole-surfactant concentrate to the stirred, cooled buffer solution. A stirring rate of at least 700 rpm is recommended. The resulting cooled suspension is immediately sonicated (10,000 to 25,000 Hz, at least 400 W) for 15–20 minutes, in 5-minute intervals. After the first 5-minute sonication, remove the ice bath and proceed with further sonication. At the end of ultrasonication, the temperature of the suspension in the hopper does not exceed 75° C.

The resultant suspension is collected in a 500-mL bottle, which is cooled immediately in the refrigerator (2–8° C.). Characteristics of particle morphology of the suspension before and after sonication were very similar to that seen in Example 1, except that in Process Category 1, Method B, the pre-sonicated material tended to form fewer and smaller aggregates which resulted in a much smaller overall particle size as measured by laser diffraction. After ultrasonication, dynamic light scattering results were typically identical to those presented in Example 1.

B. Examples of Process Category 2

Example 5

Preparation of Itraconazole Suspension (1%) with 0.75% Solutol® HR (PEG-660 12-hydroxystearate) Process Category 2, Method B

Solutol (2.25 g) and itraconazole (3.0 g) were weighed into a beaker and 36 mL of filtered N-methyl-2-pyrrolidinone (NMP) was added. This mixture was stirred under low heat (up to 40° C.) for approximately 15 minutes until the solution ingredients were dissolved. The solution was cooled to room temperature and was filtered through a 0.2-micron filter under vacuum. Two 60-mL syringes were filled with the filtered drug concentrate and were placed in a syringe pump. The pump was set to deliver approximately 1 mL/min of concentrate to a rapidly stirred (400 rpm) aqueous buffer solution. The buffer solution consisted of 22 g/L of glycerol in 5 mM tris buffer. Throughout concentrate addition, the buffer solution was kept in an ice bath at 2–3° C. At the end of the precipitation, after complete addition of concentrate to the buffer solution, about 100 mL of the suspension was centrifuged for 1 hour, the supernatant was discarded. The precipitate was resuspended in a 20% NMP solution in water, and again centrifuged for 1 hour. The material was dried overnight in a vacuum oven at 25° C. The dried material was transferred to a vial and analyzed by X-ray diffractometry using chromium radiation (see FIG. 5).

Figure 5:
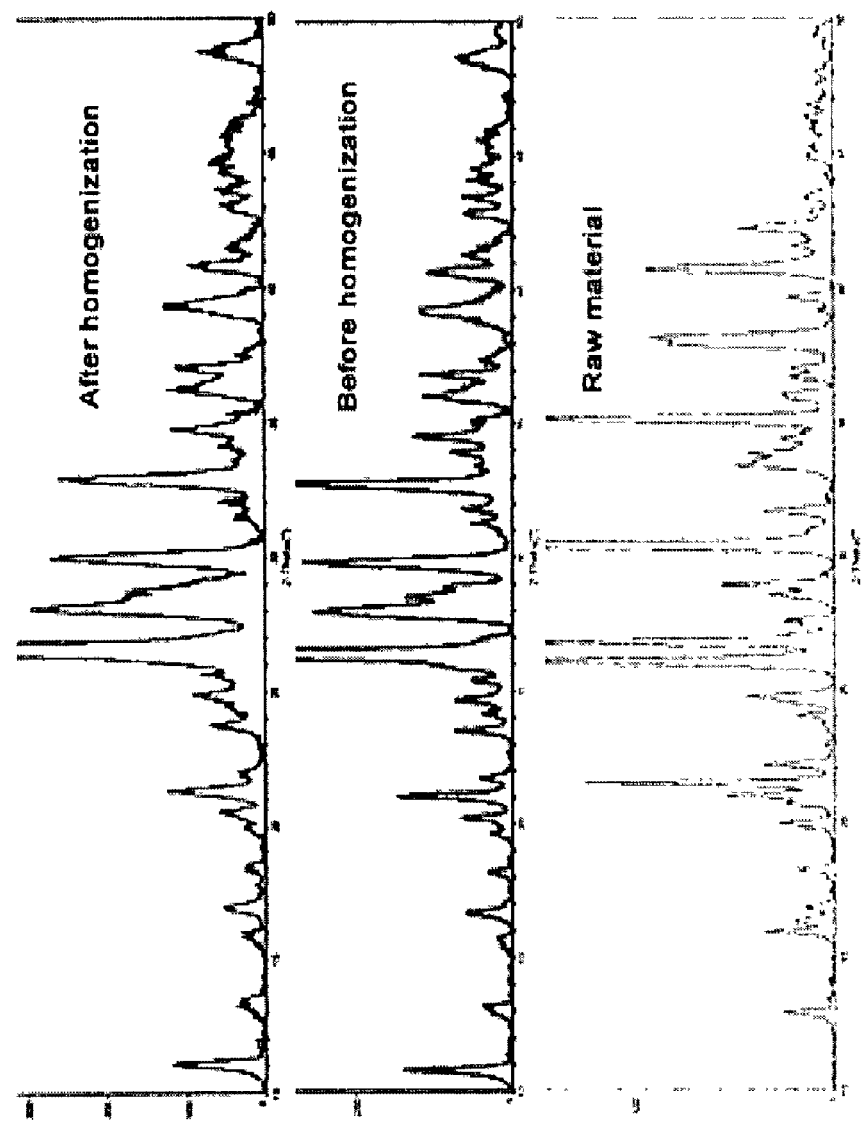
FIG. 5 is an X-Ray diffractogram of microprecipitated itraconazole with polyethylene glycol-660 12-hydroxystearate before and after homogenization.

Another 100 mL-aliquot of the microprecipitated suspension was sonicated for 30 minutes at 20,000 Hz, 80% full amplitude (full amplitude=600 W). The sonicated sample was homogenized in 3 equal aliquots each for 45 minutes (Avestin C5, 2–5° C., 15,000–20,000 psi). The combined fractions were centrifuged for about 3 hours, the supernatant removed, and the precipitate resuspended in 20% NMP. The resuspended mixture was centrifuged again (15,000 rpm at 5° C.). The supernatant was decanted off and the precipitate was vacuum dried overnight at 25° C. The precipitate was submitted for analysis by X-ray diffractometry (see FIG. 5). As seen in FIG. 5, the X-ray diffraction patterns of processed samples, before and after homogenization, are essentially identical, yet show a significantly different pattern as compared with the starting raw material. The unhomogenized suspension is unstable and agglomerates upon storage at room temperature. The stabilization that occurs as a result of homogenization is believed to arise from rearrangement of surfactant on the surface of the particle. This rearrangement should result in a lower propensity for particle aggregation.

C. Examples of Process Category

Example 6

Preparation of Carbamazepine Suspension by Use of Process Category 3, Method A with Homogenization

2.08 g of carbamazepine was dissolved into 10 mL of NMP. 1.0 mL of this concentrate was subsequently dripped at 0.1 mL/min into 20 mL of a stirred solution of 1.2% lecithin and 2.25% glycerin. The temperature of the lecithin system was held at 2–5° C. during the entire addition. The predispersion was next homogenized cold (5–15° C.) for 35 minutes at 15,000 psi. The pressure was increased to 23,000 psi and the homogenization was continued for another 20 minutes. The particles produced by the process had a mean diameter of 0.881 μm with 99% of the particles being less than 2.44 μm.

Example 7

Preparation of 1% Carbamazepine Suspension with 0.125% Solutole by Use of Process Category 3, Method B with Homogenization

A drug concentrate of 20% carbamazepine and 5% glycodeoxycholic acid (Sigma Chemical Co.) in N-methyl-2-pyrrolidinone was prepared. The microprecipitation step involved adding the drug concentrate to the receiving solution (distilled water) at a rate of 0.1 mL/min. The receiving solution was stirred and maintained at approximately 5° C. during precipitation. After precipitation, the final ingredient concentrations were 1% carbamazepine and 0.125% Solutol®. The drug crystals were examined under a light microscope using positive phase contrast (400x). The precipitate consisted of fine needles approximately 2 microns in diameter and ranging from 50–150 microns in length.

Homogenization (Avestin C-50 piston-gap homogenizer) at approximately 20,000 psi for approximately 15 minutes results in small particles, less than 1 micron in size and largely unaggregated. Laser diffraction analysis (Horiba) of the homogenized material showed that the particles had a mean size of 0.4 micron with 99% of the particles less than 0.8 micron. Low energy sonication, suitable for breaking agglomerated particles, but not with sufficient energy to cause a comination of individual particles, of the sample before Horiba analysis had no effect on the results (numbers were the same with and without sonication). This result was consistent with the absence of particle agglomeration.

Samples prepared by the above process were centrifuged and the supernatant solutions replaced with a replacement solution consisting of 0.125% Solutol®. After centrifugation and supernatant replacement, the suspension ingredient concentrations were 1% carbamazepine and 0.125% Solutol®. The samples were re-homogenized by piston-gap homogenizer and stored at 5° C. After 4 weeks storage, the suspension had a mean particle size of 0.751 with 99% less than 1.729. Numbers reported are from Horiba analysis on unsonicated samples.

Example 8

Preparation of 1% Carbamazepine Suspension with 0.06% Sodium Glycodeoxycholate and 0.06% Poloxamer 188 by Use of Process Category 3, Method B with Homogenization A drug concentrate comprising 20% carbamazepine and 5% glycodeoxycholate in N-methyl-2-pyrrolidinone was prepared. The microprecipitation step involved adding the drug concentrate to the receiving solution (distilled water) at a rate of 0.1 mL/min. Thus, this and the following examples demonstrate that adding a surfactant or other excipient to the aqueous precipitating solution in Methods A and B above is optional. The receiving solution was stirred and maintained at approximately 5° C. during precipitation. After precipitation, the final ingredient concentrations were 1% carbamazepine and 0.125% Soluto®. The drug crystals were examined under a light microscope using positive phase contrast (400×). The precipitate consisted of fine needles approximately 2 microns in diameter and ranging from 50–150 microns in length. Comparison of the precipitate with the raw material before precipitation reveals that the precipitation step in the presence of surface modifier (glycodeoxycholic acid) results in very slender crystals that are much thinner than the starting raw material (see FIG. 6).

Figure 7:
FIG. 7 shows carbamazepine microparticulate after homogenization (Avestin C-50)

Homogenization (Avestin C-50 piston-gap homogenizer) at approximately 20,000 psi for approximately 15 minutes results in small particles, less than 1 micron in size and largely unaggregated. See FIG. 7. Laser diffraction analysis (Horiba) of the homogenized material showed that the particles had a mean size of 0.4 micron with 99% of the particles less than 0.8 micron. Sonication of the sample before Horiba analysis had no effect on the results (numbers were the same with and without sonication). This result was consistent with the absence of particle agglomeration.

Samples prepared by the above process were centrifuged and the supernatant solutions replaced with a replacement solution consisting of 0.06% glycodeoxycholic acid (Sigma Chemical Co.) and 0.06% Poloxamer 188. The samples were re-homogenized by piston-gap homogenizer and stored at 5° C. After 2 weeks storage, the suspension had a mean particle size of 0.531 micron with 99% less than 1.14 micron. Numbers reported are from Horiba analysis on unsonicated samples.

Figure 6:
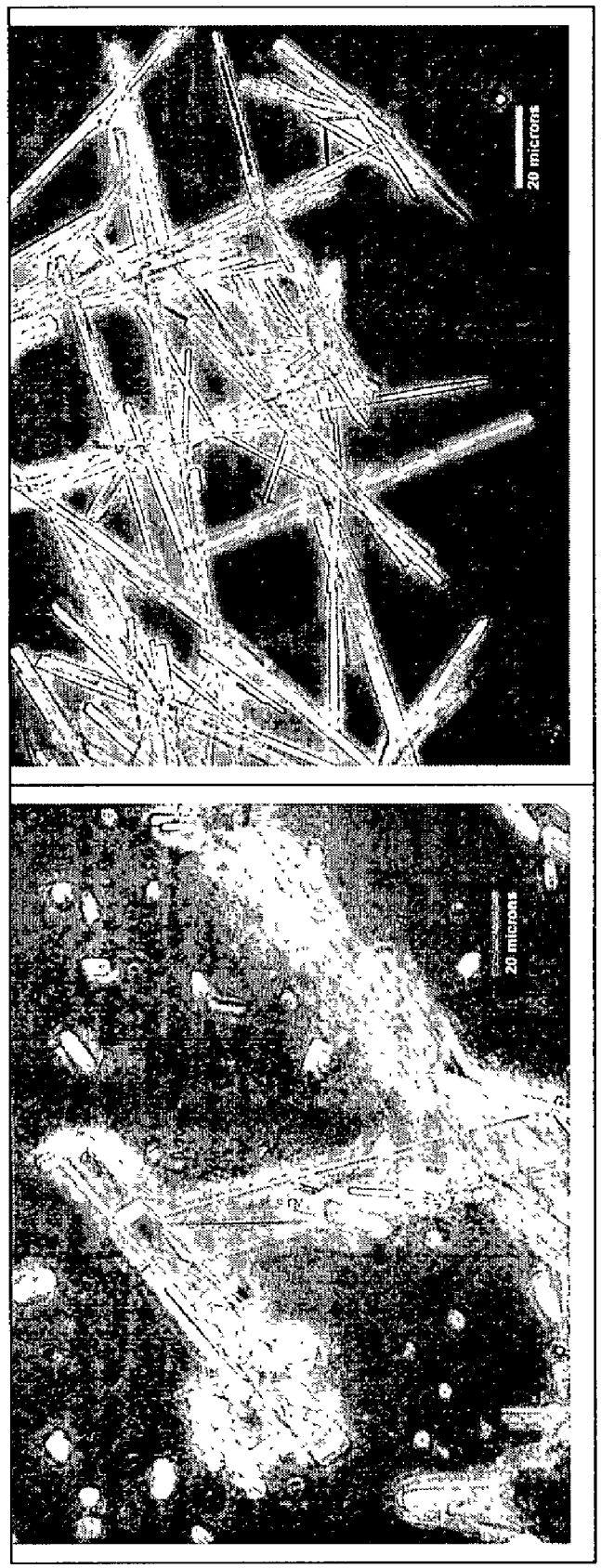
FIG. 6 shows carbamazepine crystals before homogenization.

Mathematical Analysis (Example 8) of force required to break precipitated particles as compared to force required to break particles of the starting raw material (carbamazepine):

The width of the largest crystals seen in the carbamazepine raw material (FIG. 6, picture on left) are roughly 10-fold greater than the width of crystals in the microprecipitated material (FIG. 6, picture on right). On the assumption that the ratio of crystal thickness (1:10) is proportional to the ratio of crystal width (1:10), then the moment of force required to cleave the larger crystal in the raw material should be approximately 1,000-times greater than the force needed to break the microprecipitated material, since:

$$e_L = 6PL/(Ewx^2) \quad \text{Eq. 1}$$

where, $e_L$=longitudinal strain required to break the crystal ("yield value")

P=load on beam

L=distance from load to fulcrum

E=elasticity modulus w=width of crystal x=thickness of crystal

Let us assume that L and E are the same for the raw material and the precipitated material. Additionally, let us assume that $w/w_0 = x/x_0 = 10$. Then, $(e_L)_0 = 6P_0L/(Ew_0x_0^2)$, where the '0' subscripts refer to raw material $e_L = 6PL/(Ewx^2)$, for the microprecipitate Equating $(e_L)_0$ and $e_L$, $6PL/(Ewx^2) = 6P_0L/(Ew_0x_0^2)$ After simplification, $P = P_0(w/w_0)(x/x_0)^2 = P_0(0.1)(0.1)^2 = 0.001\ P_0$ Thus, the yield force, P, required to break the microprecipitated solid is one-thousandth the required force necessary to break the starting crystalline solid. If, because of rapid precipitation, lattice defects or amorphic properties are introduced, then the modulus (E) should decrease, making the microprecipitate even easier to cleave.

Example 9

Figure 8:
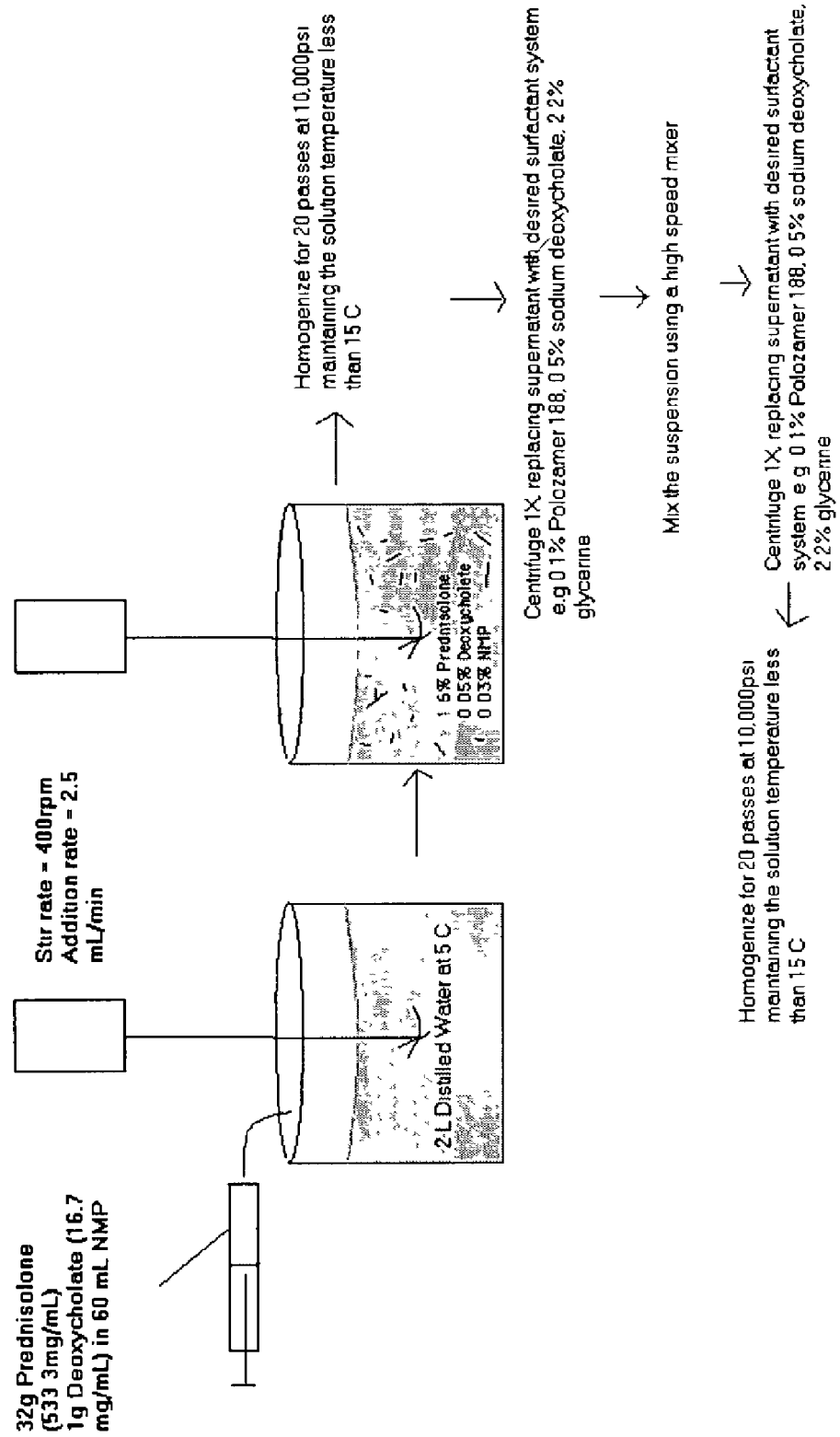
FIG. 8 is a diagram of illustrating the microprecipitation process for prednisolone.
Figure 9:
FIG. 9 is a photomicrograph of prednisolone suspension before homogenization.

Preparation of 1.6% (w/v) Prednisolone Suspension with 0.05% Sodium Deoxycholate and 3% N-methyl-2-pyrrolidinone Process Category 3, Method B A schematic of the overall manufacturing process is presented in FIG. 8. A concentrated solution of prednisolone and sodium deoxycholate was prepared. Prednisolone (32 g) and sodium deoxycholate (1 g) were added to a sufficient volume of 1-methyl 2-pyrrolidinone (NMP) to produce a final volume of 60 mL. The resulting prednisolone concentration was approximately 533.3 mg/mL and the sodium deoxycholate concentration was approximately 16.67 mg/mL. 60 mL of NMP concentrate was added to 2 L of water cooled to 5° C. at an addition rate of 2.5 mL/min while stirring at approximately 400 rpm. The resulting suspension contained slender needle-shaped crystals less than 2 μm in width (FIG. 9). The concentration contained in the precipitated suspension was 1.6% (w/v) prednisolone, 0.05% sodium deoxycholate, and 3% NMP.

Figure 10:
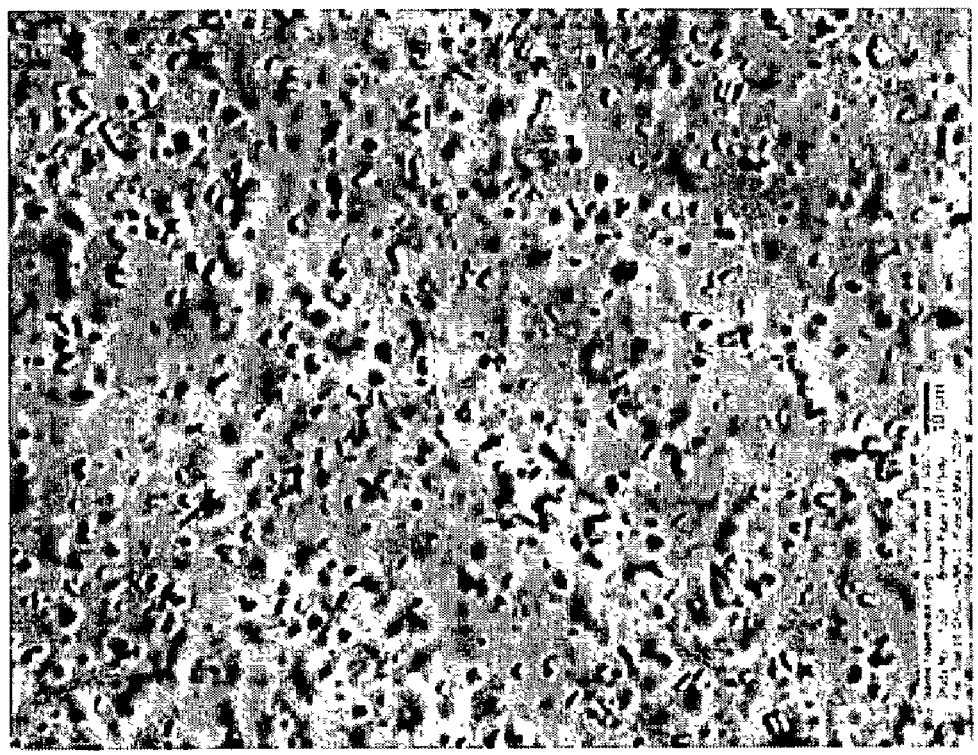
FIG. 10 is a photomicrograph of prednisolone suspension after homogenization.

The precipitated suspension was pH adjusted to 7.5–8.5 using sodium hydroxide and hydrochloric acid then homogenized (Avestin C-50 piston-gap homogenizer) for 10 passes at 10,000 psi. The NMP was removed by performing 2 successive centrifugation steps replacing the supernatant each time with a fresh surfactant solution, which contained the desired concentrations of surfactants needed to stabilize the suspension (see Table 2). The suspension was homogenized for another 10 passes at 10,000 psi. The final suspension contained particles with a mean particle size of less than 1 μm, and 99% of particles less than 2 μm. FIG. 10 is a photomicrograph of the final prednisolone suspension after homogenization.

A variety of different surfactants at varying concentrations were used in the centrifugation/surfactant replacement step (see Table 2). Table 2 lists combinations of surfactants that were stable with respect to particle size (mean <1 μm, 99%<2 μm), pH (6–8), drug concentration (less than 2% loss) and re-suspendability (resuspended in 60 seconds or less).

Notably this process allows for adding the active compound to an aqueous diluent without the presence of a surfactant or other additive. This is a modification of process Method B in FIG. 2.

modifiers were added. The surfactant system was buffered at pH=8.0 with 5 mM tris buffer and the temperature was held at 0° to 5° C. during the entire precipitation process. The post-precipitated dispersion was next homogenized cold (5–15° C.) for 20 passes at 10,000 psi. Following homogenization, the NMP was removed by centrifuging the suspension, removing the supernatant, and replacing the supernatant with fresh surfactant solution. This post-centrifuged suspension was then rehomogenized cold (5–15° C.) for another 20 passes at 10,000 psi. The particles produced by this process had a mean diameter of 0.927 μm with 99% of the particles being less than 2.36 μm.

Example 11

Preparation of Nabumetone Suspension by Use of Process Category 3, Method B with Homogenization Surfactant (2.2 g of poloxamer 188) was dissolved in 6 mL of N-methyl-2-pyrrolidinone. This solution was stirred at 45° C. for 15 minutes, after which 1.0 g of nabumetone was added. The drug dissolved rapidly. Diluent was prepared which consisted of 5 mM tris buffer with 2.2% glycerol, and adjusted to pH 8. A 100-mL portion of diluent

TABLE 2

List of stable prednisolone suspensions prepared by microprecipitation process of FIG. 8 (Example 9)

| | | | | | 2 Months | | | | | | |
|---|---|---|---|---|---|---|---|---|---|---|---|
| | Initial | | 40° C. | | 5° C. | | 25° C. | | 40° C. | | |
| Formulation | Mean | >99% | Mean | >99% | Mean | >99% | Mean | >99% | Mean | >99% | % Loss* |
| 1.6% prednisolone, 0.6% phospholipids, 0.5% sodium deoxycholate, 5 mM TRIS, 2.2% glycerol ** | 0.79 | 1.65 | 0.84 | 1.79 | 0.83 | 1.86 | 0.82 | 1.78 | 0.82 | 1.93 | <2% |
| 1.6% prednisolone, 0.6% Solutol ®, 0.5% sodium deoxycholate, 2.2% glycerol | 0.77 | 1.52 | 0.79 | 1.67 | 0.805 | 1.763 | 0.796 | 1.693 | 0.81 | 1.633 | <2% |
| 1.6% prednisolone, 0.1% poloxamer 188, 0.5% sodium deoxycholate, 2.2% glycerol | 0.64 | 1.16 | 0.82 | 1.78 | 0.696 | 1.385 | 0.758 | 1.698 | 0.719 | 1.473 | <2% |
| 1.6% prednisolone, 5% phospholipids, 5 mM TRIS, 2.2% glycerol | 0.824 | 1.77 | 0.87 | 1.93 | 0.88 | 1.95 | 0.869 | 1.778 | 0.909 | 1.993 | <2% |

*Difference in itraconazole concentration between samples stored for 2 months at 5 and 25° C.
** Stable through at least 6 months.

Particle sizes (by laser light scattering), in microns:
5° C.: 0.80 (mean), 1.7 (99%)
25° C.: 0.90 (mean); 2.51 (99%)
40° C.: 0.99 (mean); 2.03 (99%)
Difference in itraconazole concentration between samples stored at 5 and 25° C.: <2%

Example 10

Preparation of Prednisolone Suspension by Use of Process Category 3, Method A with Homogenization 32 g of prednisolone was dissolved into 40 mL of NMP. Gentle heating at 40–50° C. was required to effect dissolution. The drug NMP concentrate was subsequently dripped at 2.5 mL/min into 2 liters of a stirred solution that consisted of 0.1% lecithin and 2.2% glycerin. No other surface was cooled in an ice bath. The drug concentrate was slowly added (approximately 0.8 mL/min) to the diluent with vigorous stirring. This crude suspension was homogenized at 15,000 psi for 30 minutes and then at 20,000 psi for 30 minutes (temperature=5° C.). The final nanosuspension was found to be 930 nm in effective mean diameter (analyzed by laser diffraction). 99% of the particles were less than approximately 2.6 microns.

Example 12

Preparation of Nabumetone Suspension by Use of Process Category 3, Method B with Homogenization and the Use of Solutol® HS 15 as the Surfactant. Replacement of Supernatant Liquid with a Phospholipid Medium Nabumetone (0.987 grams) was dissolved in 8 mL of N-methyl-2-pyrrolidinone. To this solution was added 2.2 grams of Solutol® HS 15. This mixture was stirred until complete dissolution of the surfactant in the drug concentrate. Diluent was prepared, which consisted of 5 mM tris buffer with 2.2% glycerol, and which was adjusted to pH 8. The diluent was cooled in an ice bath, and the drug concentrate was slowly added (approximately 0.5 mL/min) to the diluent with vigorous stirring. This crude suspension was homogenized for 20 minutes at 15,000 psi, and for 30 minutes at 20,000 psi.

The suspension was centrifuged at 15,000 rpm for 15 minutes and the supernatant was removed and discarded. The remaining solid pellet was resuspended in a diluent consisting of 1.2% phospholipids. This medium was equal in volume to the amount of supernatant removed in the previous step. The resulting suspension was then homogenized at approximately 21,000 psi for 30 minutes. The final suspension was analyzed by laser diffraction and was found to contain particles with a mean diameter of 542 nm, and a 99% cumulative particle distribution sized less than 1 micron.

Example 13

Preparation of 1% Itraconazole Suspension with Poloxamer with Particles of a Mean Diameter of Approximately 220 nm Itraconazole concentrate was prepared by dissolving 10.02 grams of itraconazole in 60 mL of N-methyl-2-pyrrolidinone. Heating to 70° C. was required to dissolve the drug. The solution was then cooled to room temperature. A portion of 50 mM tris(hydroxymethyl)aminomethane buffer (tris buffer) was prepared and was pH adjusted to 8.0 with 5M hydrochloric acid. An aqueous surfactant solution was prepared by combining 22 g/L poloxamer 407, 3.0 g/L egg phosphatides, 22 g/L glycerol, and 3.0 g/L sodium cholate dihydrate. 900 mL of the surfactant solution was mixed with 100 mL of the tris buffer to provide 1000 mL of aqueous diluent.

The aqueous diluent was added to the hopper of the homogenizer (APV Gaulin Model 15MR-8TA), which was cooled by using an ice jacket. The solution was rapidly stirred (4700 rpm) and the temperature was monitored. The itraconazole concentrate was slowly added, by use of a syringe pump, at a rate of approximately 2 mL/min. Addition was complete after approximately 30 minute. The resulting suspension was stirred for another 30 minutes while the hopper was still being cooled in an ice jacket, and an aliquot was removed for analysis by light microscopy any dynamic light scatting. The remaining suspension was subsequently homogenized for 15 minutes at 10,000 psi. By the end of the homogenization the temperature had risen to 74° C. The homogenized suspension was collected in a 1-L Type I glass bottle and sealed with a rubber closure. The bottle containing suspension was stored in a refrigerator at 5° C.

A sample of the suspension before homogenization showed the sample to consist of both free particles, clumps of particles, and multilamellar lipid bodies. The free particles could not be clearly visualized due to Brownian motion; however, many of the aggregates appeared to consist of amorphous, non-crystalline material.

Figure 11:
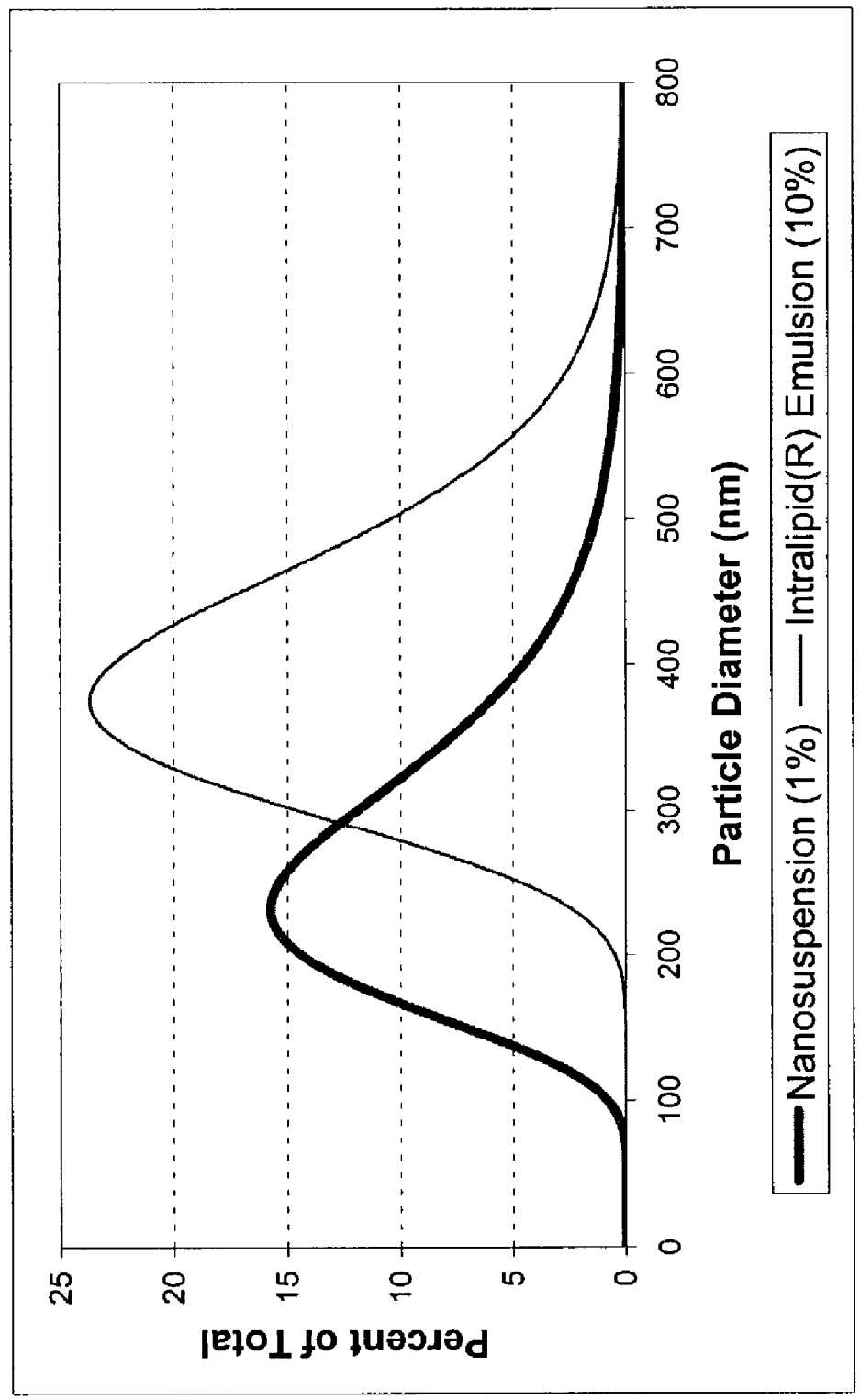
FIG. 11 illustrates a comparison of size distributions of nanosuspensions (this invention) and commercial fat emulsion.

The homogenized sample contained free submicron particles having excellent size homogeneity without visible lipid vesicles. Dynamic light scattering showed a monodisperse logarithmic size distribution with a median diameter of approximately 220 nm. The upper 99% cumulative size cutoff was approximately 500 nm. FIG. 11 shows a comparison of the size distribution of the prepared nanosuspension with that of a typical parenteral fat emulsion product (10% Intralipid®, Pharmacia).

Example 14

Preparation of 1% Itraconazole Nanosuspension with Hydroxyethylstarch

Preparation of Solution A: Hydroxyethylstarch (1 g, Ajinomoto) was dissolved in 3 mL of N-methyl-2-pyrrolidinone (NMP). This solution was heated in a water bath to 70–80° C. for 1 hour. In another container was added 1 g of itraconazole (Wyckoff). Three mL of NMP were added and the mixture heated to 70–80° C. to effect dissolution (approximately 30 minutes). Phospholipid (Lipoid S-100) was added to this hot solution. Heating was continued at 70–90° C. for 30 minutes until all of the phospholipid was dissolved. The hydroxyethylstarch solution was combined with the itraconazole/phospholipid solution. This mixture was heated for another 30 minutes at 80–95° C. to dissolve the mixture.

Addition of Solution A to Tris Buffer: Ninety-four (94) mL of 50 mM tris(hydroxymethyl)aminomethane buffer was cooled in an ice bath. As the tris solution was being rapidly stirred, the hot Solution A (see above) was slowly added dropwise (less than 2 cc/minute).

After complete addition, the resulting suspension was sonicated (Cole-Parmer Ultrasonic Processor-20,000 Hz, 80% amplitude setting) while still being cooled in the ice bath. A one-inch solid probe was utilized. Sonication was continued for 5 minutes. The ice bath was removed, the probe was removed and retuned, and the probe was again immersed in the suspension. The suspension was sonicated again for another 5 minutes without the ice bath. The sonicator probe was once again removed and retuned, and after immersion of the probe the sample was sonicated for another 5 minutes. At this point, the temperature of the suspension had risen to 82° C. The suspension was quickly cooled again in an ice bath and when it was found to be below room temperature it was poured into a Type I glass bottle and sealed. Microscopic visualization of the particles indicated individual particle sizes on the order of one micron or less.

After one year of storage at room temperature, the suspension was reevaluated for particle size and found to have a mean diameter of approximately 300 nm.

Example 15

Prophetic Example of Method A Using HES

The present invention contemplates preparing a 1% itraconazole nanosuspension with hydroxyethylstarch utilizing Method A by following the steps of Example 14 with the exception the HES would be added to the tris buffer solution instead of to the NMP solution. The aqueous solution may have to be heated to dissolve the HES.

Example 16

Seeding During Homogenization to Convert a Less Stable Polymorph to a More Stable Polymorph Preparation of Starting Material. An itraconazole nanosuspension was prepared by a microprecipitation-homogenization method as follows. Itraconazole (3 g) and Solutol HS-15 (2.25 g) were dissolved in 36 mL of N-methyl-2-pyrrolidinone (NMP) with low heat and stirring to form a drug concentrate solution. The solution was cooled to room temperature and filtered through a 0.2 μm nylon filter under vacuum to remove undissolved drug or particulate matter. The solution was viewed under polarized light to ensure that no crystalline material was present after filtering. The drug concentrate solution was then added at 1.0 mL/minute to approximately 264 mL of an aqueous buffer solution (22 g/L glycerol in 5 mM tris buffer). The aqueous solution was kept at 2–3° C. and was continuously stirred at approximately 400 rpm during the drug concentrate addition. Approximately 100 mL of the resulting suspension was centrifuged and the solids resuspended in a pre-filtered solution of 20% NMP in water. This suspension was re-centrifuged and the solids were transferred to a vacuum oven for overnight drying at 25° C. The resulting solid sample was labeled SMP 2 PRE.

Figure 12A:
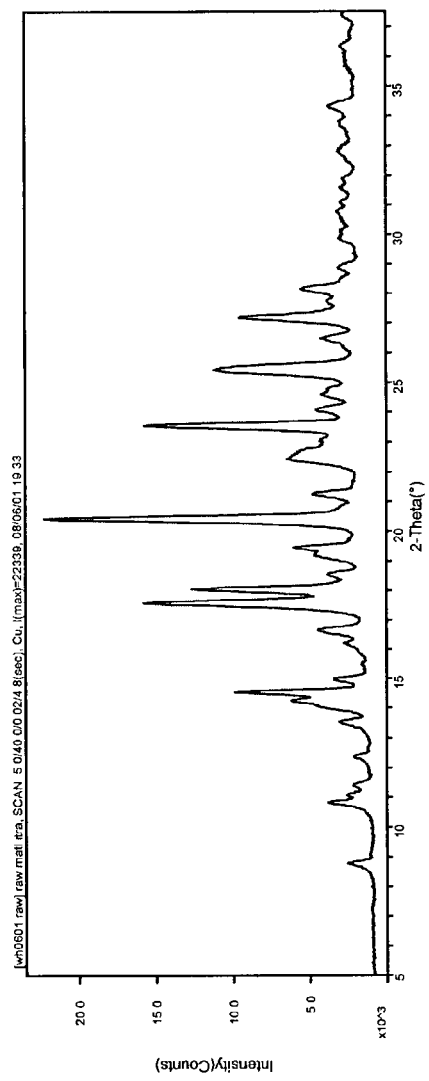
FIG. 12a shows the X-ray powder diffraction patterns for raw material itraconazole.
Figure 12B:
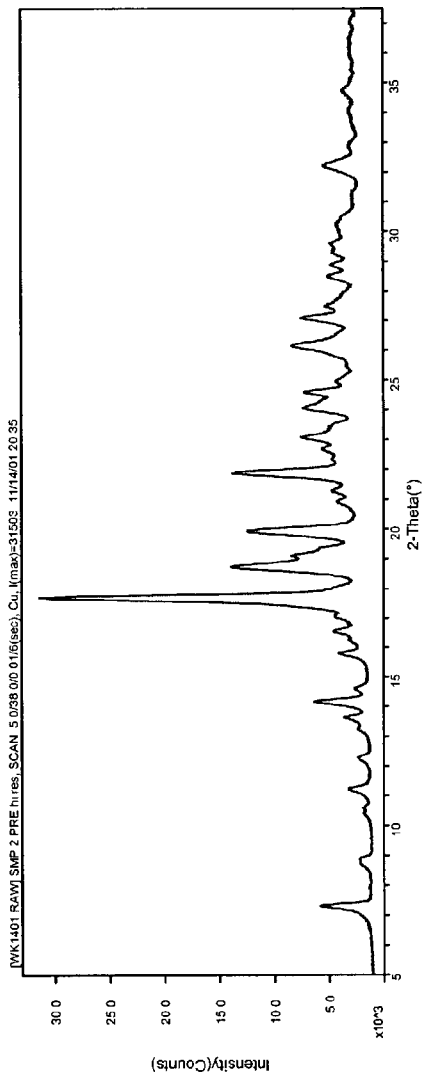
FIG. 12b shows the X-ray powder diffraction patterns for SMP-2-PRE (Example 16)

Characterization of Starting Material. The sample SMP 2 PRE and a sample of the raw material itraconazole were analyzed using powder X-ray diffractometry. The measurements were performed using a Rigaku MiniFlex+instrument with a copper target, Kβ filter, voltage=30 kV and current=40 mA. Data was collected using a step size of 0.02° 2-theta and scan speed of 0.25° 2-theta/minute between 5° and 38° 2-theta. The resulting powder diffraction patterns are shown in FIG. 12. The patterns show that SMP-2-PRE (FIG. 12b) is significantly different from the raw material (FIG. 12a), suggesting the presence of a different polymorph or a pseudopolymorph. The X-ray powder diffraction pattern for SMP-2-PRE exhibits peaks expressed in degrees 2-theta consistent with those listed in Table 3.

TABLE 3

Peaks in degrees 2-theta of the X-ray powder diffraction pattern of SMP-2-PRE

| 2-Theta | d(A) | I% |
|---|---|---|
| 7.310 | 12.0829 | 16.4 |
| 8.880 | 9.9497 | 4.0 |
| 10.386 | 8.5100 | 1.1 |
| 10.589 | 8.3475 | 2.4 |
| 11.210 | 7.8864 | 6.7 |
| 12.276 | 7.2038 | 3.8 |
| 13.210 | 6.6967 | 2.6 |
| 13.618 | 6.4968 | 6.1 |
| 14.148 | 6.2549 | 15.7 |
| 14.600 | 6.0620 | 3.5 |
| 15.773 | 5.6138 | 6.4 |
| 16.529 | 5.3587 | 6.1 |
| 17.682 | 5.0118 | 100.0 |
| 18.722 | 4.7358 | 37.8 |
| 19.100 | 4.6429 | 17.5 |
| 19.931 | 4.4510 | 32.4 |
| 20.910 | 4.2448 | 3.3 |
| 21.290 | 4.1700 | 4.0 |
| 21.870 | 4.0606 | 34.0 |
| 23.100 | 3.8472 | 13.2 |
| 24.050 | 3.6973 | 13.7 |
| 24.600 | 3.6159 | 14.4 |
| 24.940 | 3.5673 | 2.5 |
| 26.140 | 3.4062 | 17.6 |
| 27.080 | 3.2900 | 14.4 |
| 27.490 | 3.2420 | 6.9 |
| 28.500 | 3.1293 | 6.6 |
| 28.880 | 3.0889 | 4.6 |
| 29.271 | 3.0486 | 3.8 |
| 29.599 | 3.0155 | 4.6 |
| 30.241 | 2.9530 | 3.2 |
| 32.210 | 2.7768 | 10.4 |
| 32.919 | 2.7186 | 1.6 |
| 34.740 | 2.5801 | 3.3 |

Figure 18A:
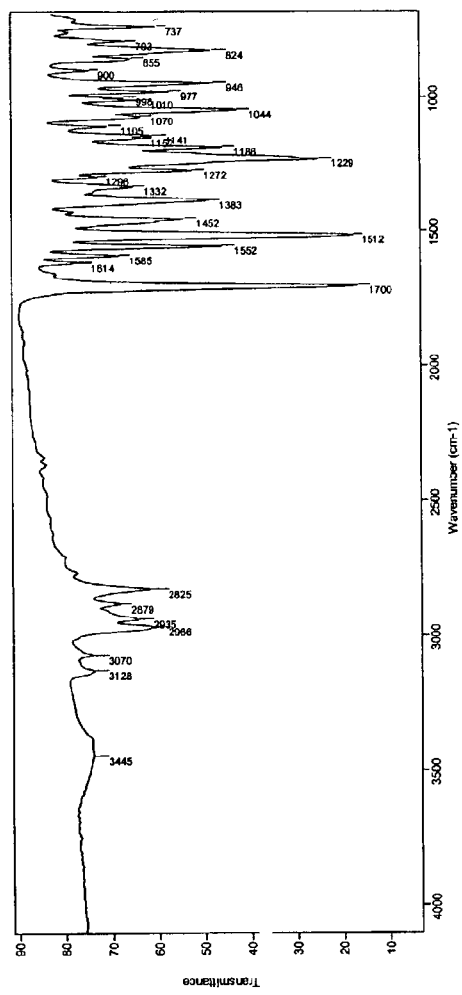
FIG. 18a is the FTIR spectrum of the raw material of itraconazole.
Figure 18B:
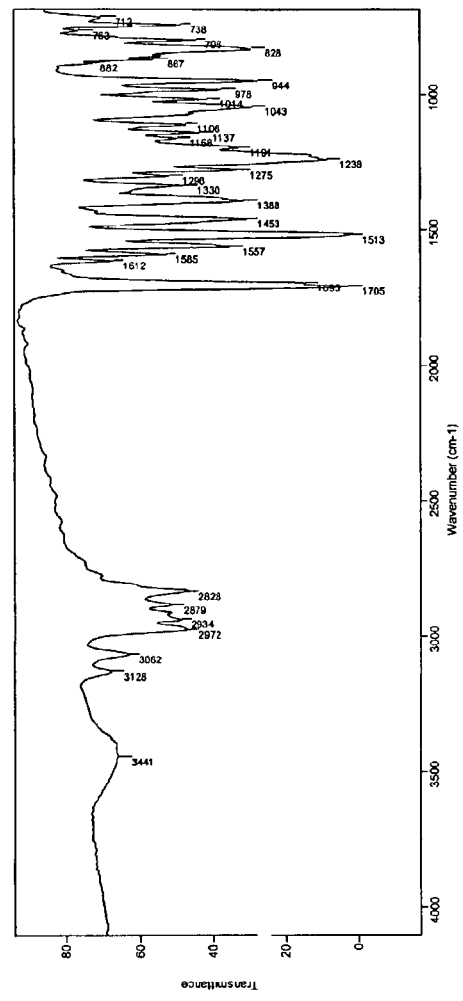
FIG. 18b is the FTIR spectrum of SMP-2-PRE.

Fourier transform infrared (FTIR) spectra of the polymorphic forms of itraconazole are shown in FIGS. 18a and 18b. FIG. 18a is the FTIR spectrum of the raw material of itraconazole, and FIG. 18b is the FTIR spectrum of SMP-2-PRE.

Figure 13A:
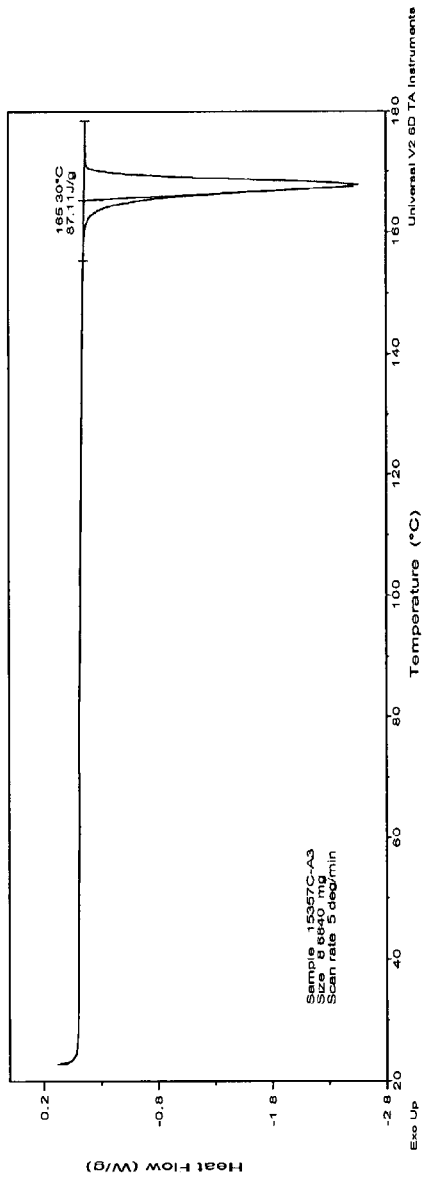
FIG. 13a shows the DSC trace for raw material itraconazole.

Differential scanning calorimetry (DSC) traces for the samples are shown in FIG. 13. Both samples were heated at 2°/min to 180° C. in hermetically sealed aluminum pans.

The trace for the raw material itraconazole (FIG. 13a) shows a sharp endotherm at approximately 165° C. and an enthalpy of fusion of approximately 87 J/g.

The trace for SMP 2 PRE (FIG. 13b) exhibits an endotherm at approximately 153° C. and an enthalpy of fusion of approximately 68 J/g. This result, in combination with the powder X-ray diffraction patterns and FTIP specta, suggests that SMP 2 PRE is a new polymorph that is less stable than polymorph present in the raw material.

Figure 14:
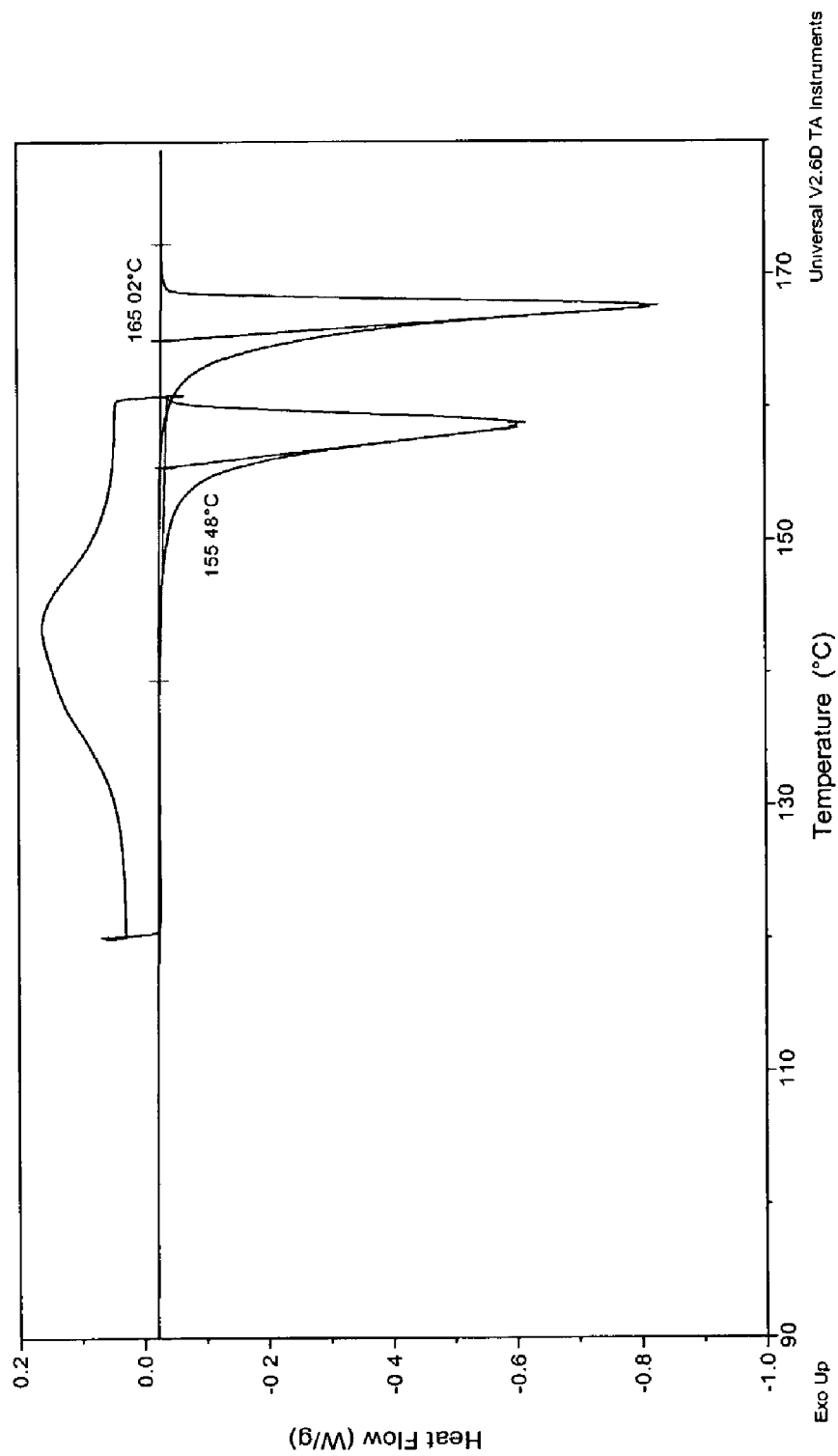
FIG. 14 illustrates the DSC trace for SMP-2-PRE showing the melt of the less stable polymorph upon heating to 160° C., a recrystallization event upon cooling, and the subsequent melting of the more stable polymorph upon reheating to 180° C. (Example 16)

Further evidence for this conclusion is provided by the DSC trace in FIG. 14, which shows that upon heating SMP 2 PRE through the first transition, then cooling and reheating, the less stable polymorph melts and recrystallizes to form the more stable polymorph.

Conversion of Starting Material to a More Stable Polymorph. A suspension was prepared by combining 0.2 g of the solid SMP 2 PRE and 0.2 g of raw material itraconazole with distilled water to a final volume of 20 mL (seeded sample). The suspension was stirred until all the solids were wetted. A second suspension was prepared in the same manner but without adding the raw material itraconazole (unseeded sample). Both suspensions were homogenized at approximately 18,000 psi for 30 minutes. Final temperature of the suspensions after homogenization was approximately 30° C. The suspensions were then centrifuged and the solids dried for approximately 16 hours at 30° C.

Figure 15:
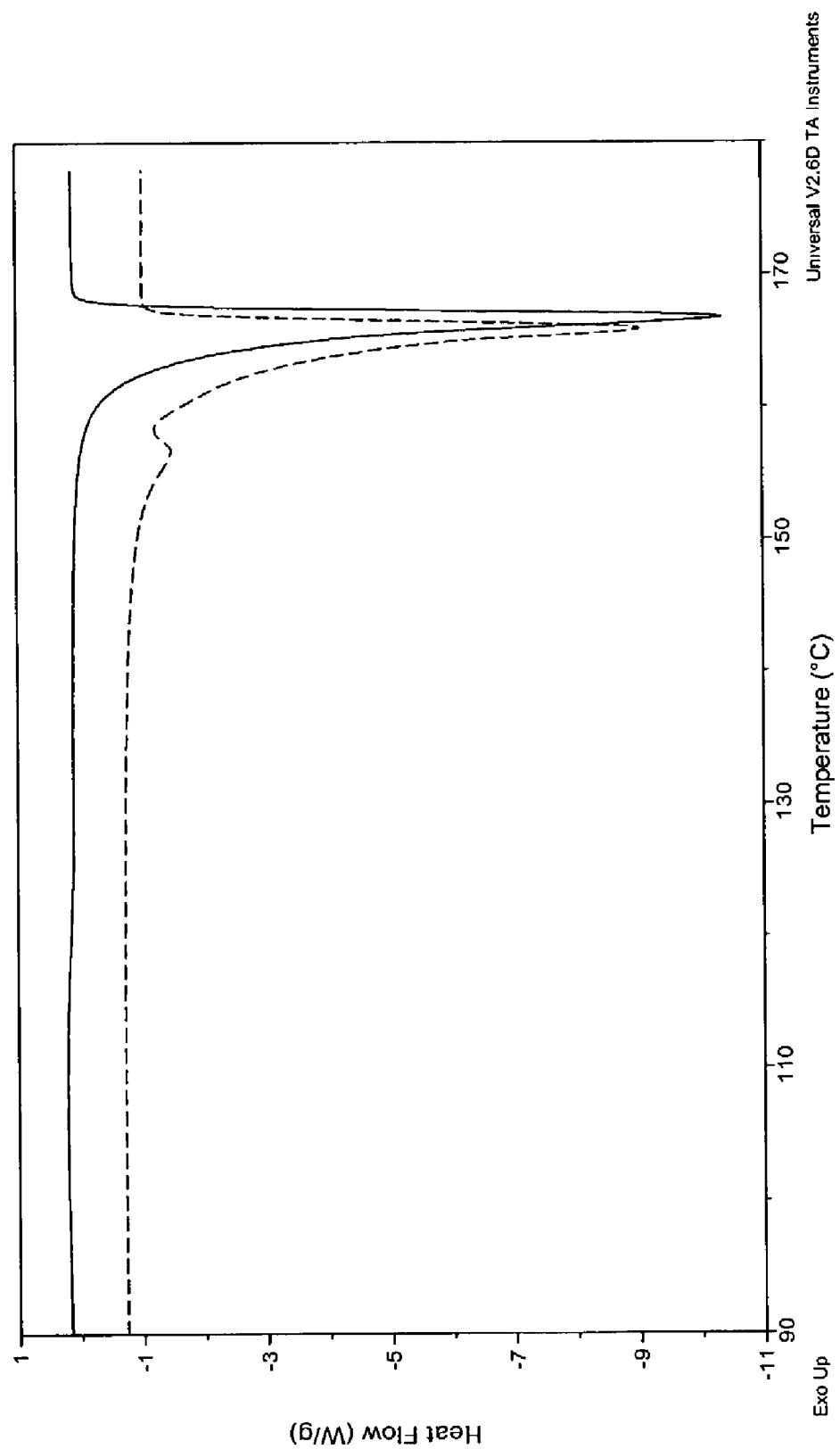
FIG. 15 illustrates a comparison of SMP-2-PRE samples after homogenization. Solid line=sample seeded with raw material itraconazole. Dashed line=unseeded sample. The solid line has been shifted by 1 W/g for clarity (Example 16)

FIG. 15 shows the DSC traces of the seeded and unseeded samples. The heating rate for both samples was 2°/min to 180° C. in hermetically sealed aluminum pans. The trace for the unseeded sample shows two endotherms, indicating that the less stable polymorph is still present after homogenization. The trace for the seeded sample shows that seeding and homogenization causes the conversion of the solids to the stable polymorph. Therefore, seeding appears to influence the kinetics of the transition from the less stable to the more stable polymorphic form.

Example 17

Seeding During Precipitation to Preferentially Form a Stable Polymorph Sample Preparation.

An itraconazole-NMP drug concentrate was prepared by dissolving 1.67 g of itraconazole in 10 mL of NMP with stirring and gentle heating. The solution was filtered twice using 0.2 μm syringe filters. Itraconazole nanosuspensions were then prepared by adding 1.2 mL of the drug concentrate to 20 mL of an aqueous receiving solution at approx. 3° C. and stirring at approx. 500 rpm. A seeded nanosuspension was prepared by using a mixture of approx. 0.02 g of raw material itraconazole in distilled water as the receiving solution. An unseeded nanosuspension was prepared by using distilled water only as the receiving solution. Both suspensions were centrifuged, the supernatants decanted, and the solids dried in a vacuum oven at 30° C. for approximately 16 hours.

Figure 16:
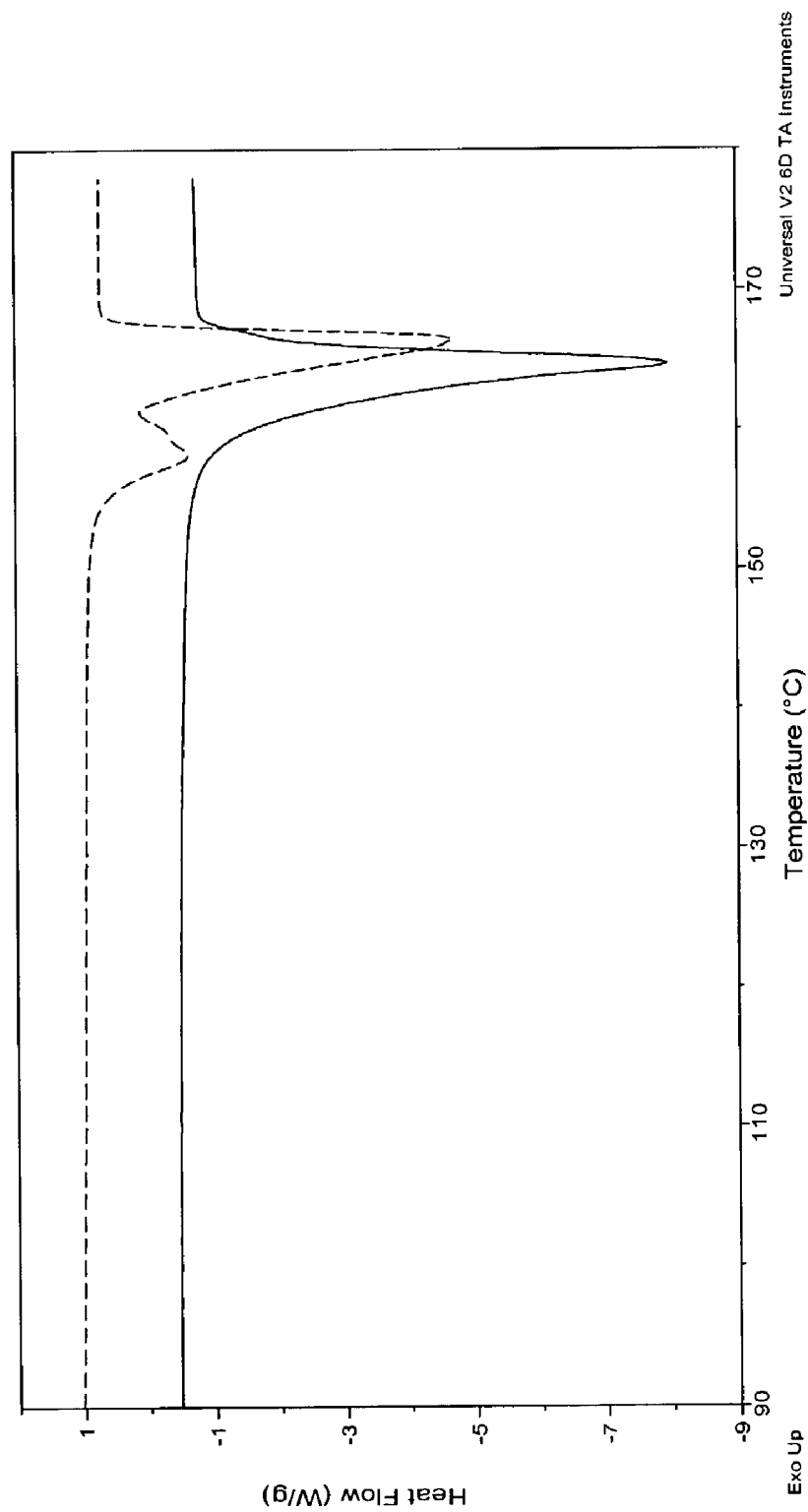
FIG. 16 illustrates the effect of seeding during precipitation. Dashed line=unseeded sample, solid line=sample seeded with raw material itraconazole. The unseeded trace (dashed line) has been shifted upward by 1.5 W/g for clarity.

Sample characterization. FIG. 16 shows a comparison of the DSC traces for the solids from the seeded and unseeded suspensions. The samples were heated at 2°/min to 180° C.

in hermetically sealed aluminum pans. The dashed line represents the unseeded sample, which shows two endotherms, indicating the presence of a polymorphic mixture. The solid line represents the seeded sample, which shows only one endotherm near the expected melting temperature of the raw material, indicating that the seed material induced the exclusive formation of the more stable polymorph.

Example 18

Polymorph Control by Seeding the Drug Concentrate Sample Preparation.

The solubility of itraconazole in NMP at room temperature (approximately 22° C.) was experimentally determined to be 0.16 g/mL. A 0.20 g/mL drug concentrate solution was prepared by dissolving 2.0 g of itraconazole and 0.2 g Poloxamer 188 in 10 mL NMP with heat and stirring. This solution was then allowed to cool to room temperature to yield a supersaturated solution. A microprecipitation experiment was immediately performed in which 1.5 mL of the drug concentrate was added to 30 mL of an aqueous solution containing 0.1% deoxycholate, 2.2% glycerol. The aqueous solution was maintained at ~2° C. and a stir rate of 350 rpm during the addition step. The resulting presuspension was homogenized at ~13,000 psi for approx. 10 minutes at 50° C. The suspension was then centrifuged, the supernatant decanted, and the solid crystals dried in a vacuum oven at 30° C. for 135 hours.

The supersaturated drug concentrate was subsequently aged by storing at room temperature in order to induce crystallization. After 12 days, the drug concentrate was hazy, indicating that crystal formation had occurred. An itraconazole suspension was prepared from the drug concentrate, in the same manner as in the first experiment, by adding 1.5 mL to 30 mL of an aqueous solution containing 0.1% deoxycholate, 2.2% glycerol. The aqueous solution was maintained at ~5° C. and a stir rate of 350 rpm during the addition step. The resulting presuspension was homogenized at ~13,000 psi for approx. 10 minutes at 50° C. The suspension was then centrifuged, the supernatant decanted, and the solid crystals dried in a vacuum oven at 30° C. for 135 hours.

Figure 17:
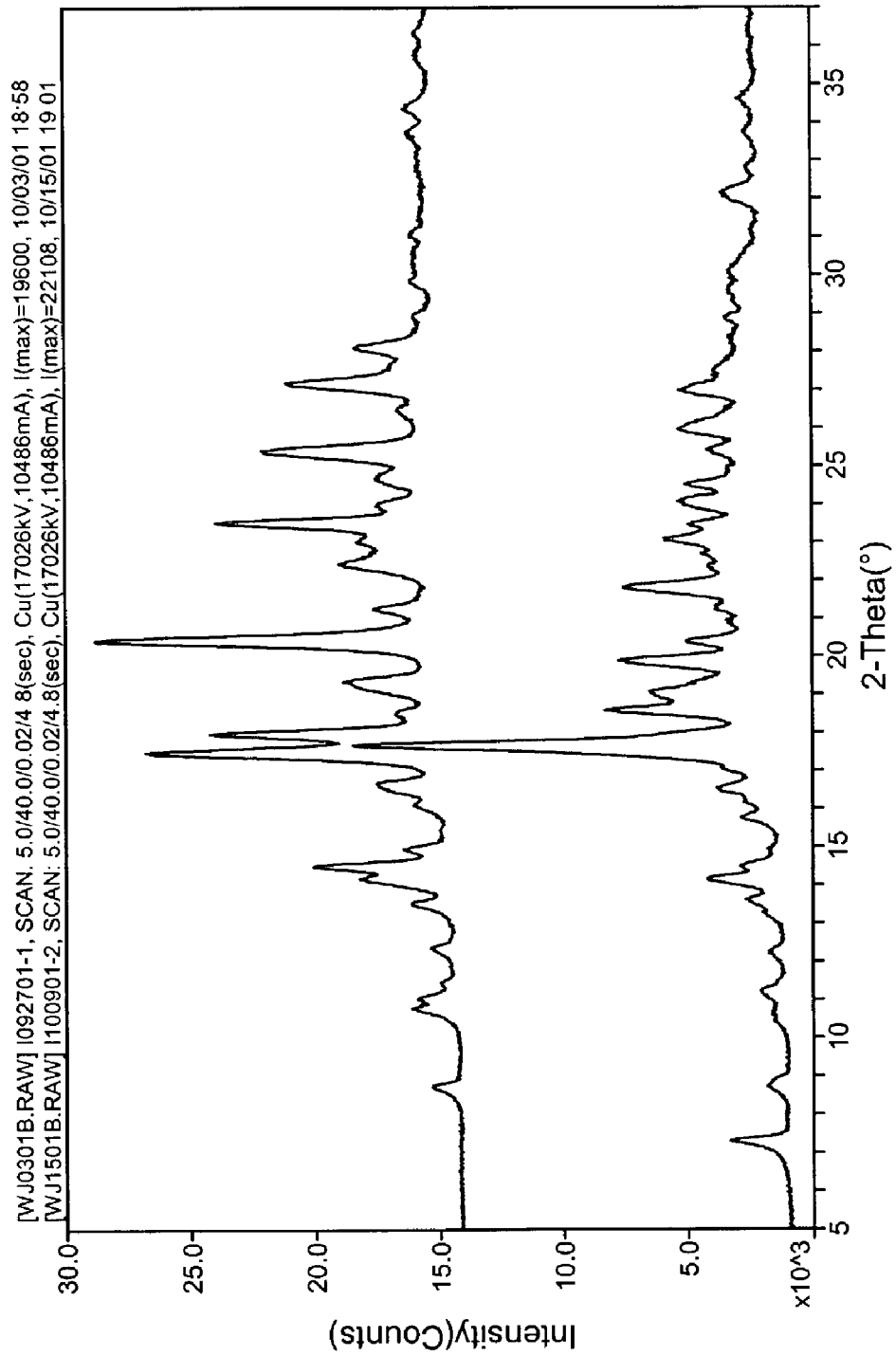
FIG. 17 illustrates the effect of seeding the drug concentrate through aging. Top X-ray diffraction pattern is for crystals prepared from fresh drug concentrate, and is consistent with the stable polymorph (see FIG. 12a). Bottom pattern is for crystals prepared from aged (seeded) drug concentrate, and is consistent with the metastable polymorph (see FIG. 12b). The top pattern has been shifted upward for clarity.

Sample characterization. X-ray powder diffraction analysis was used to determine the morphology of the dried crystals. The resulting patterns are shown in FIG. 17. The crystals from the first experiment (using fresh drug concentrate) were determined to consist of the more stable polymorph. In contrast, the crystals from the second experiment (aged drug concentrate) were predominantly composed of the less stable polymorph, with a small amount of the more stable polymorph also present.

Example 19

Preparation of a Nanosuspension Containing the New Polymorph of Itraconazole

Itraconazole (10 g) was dissolved in 35.1 g of 85% lactic acid using mild heat and stirring to yield a drug concentrate solution. The drug concentrate was cooled to room temperature and then slowly added to 1 L of an aqueous solution containing 11 g/L Poloxamer 188, 11 g/L Poloxamer 407, and 22 g/L glycerol. During addition the aqueous phase was stirred at 700 rpm. The resulting suspension was homogenized using a piston-gap homogenizer at 10,000 psi. The suspension was then centrifuged at 10,000 rpm for 10 minutes. The supernatant was decanted and replaced with fresh aqueous solution, and the solids resuspended. The suspension was then re-homogenized at 10,000 psi.

The resulting suspension was then stored at 5° C. for 14 months. Following the storage period, a 20 mL sample of the suspension was centrifuged at 20,000 rpm for 1 hour. The solids were collected and dried in a vacuum oven at 30° C. The crystalline solids exhibited a X-ray powder diffraction pattern consistent with that shown in FIG. 12b, and a DSC trace consistent with that shown in FIG. 13b.

While specific embodiments have been illustrated and described, numerous modifications come to mind without departing from the spirit of the invention and the scope of protection is only limited by the scope of the accompanying claims.

What is claimed is:

1. A crystalline polymorph of itraconazole having substantially the same X-ray diffractogram as shown in FIG. 12b characterized by peaks at values of two theta of approximately 7.3°, 19.9°, 21.9°, 26.1°, and 32.2°.

2. The polymorph of itraconazole of claim 1 further having an FTIR spectrum substantially the same as shown in FIG. 18b.

Figure 13B:
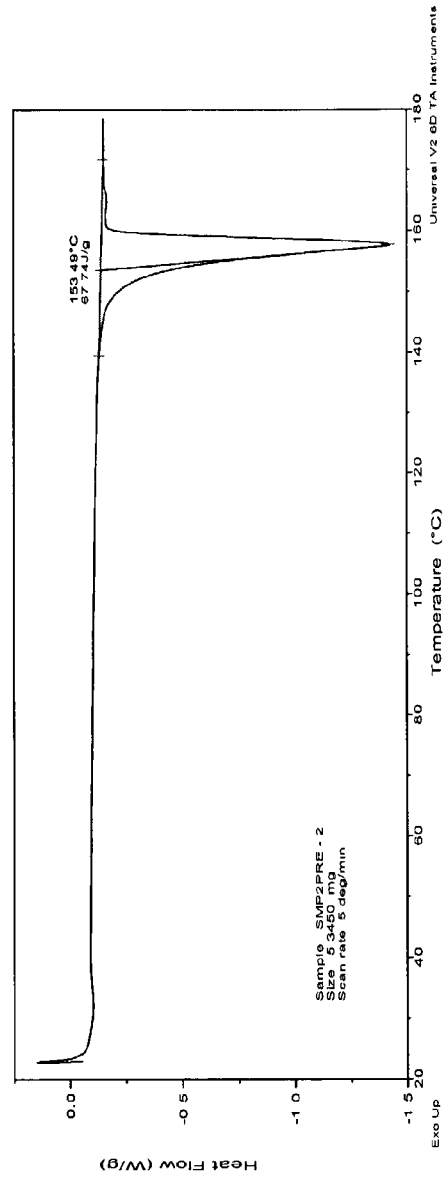
FIG. 13b shows the DSC trace for SMP-2-PRE (Example 16)

3. The polymorph of itraconazole of claim 1 further having a DSC profile substantially the same as shown in FIG. 13b.

* * * * *

UNITED STATES PATENT AND TRADEMARK OFFICE
CERTIFICATE OF CORRECTION

PATENT NO. : 7,193,084 B2
APPLICATION NO. : 10/213352
DATED : March 20, 2007
INVENTOR(S) : Werling et al.

It is certified that error appears in the above-identified patent and that said Letters Patent is hereby corrected as shown below:

Column 1, Line 8, delete "Oct." and insert --Sept.--

Column 11, Line 61, insert --.-- after "sources"

Column 16, Line 51, delete "Solutole" and insert --Solutol®--

Column 17, Line 40, delete "Soluto" and insert --Solutol--

Column 25, Line 12, delete "Sample Preparation."

Column 25, Line 14, insert -- Sample Preparation. --

Signed and Sealed this

Eighth Day of May, 2007

JON W. DUDAS
*Director of the United States Patent and Trademark Office*